(12) United States Patent
Komers et al.

(10) Patent No.: US 10,864,197 B2
(45) Date of Patent: Dec. 15, 2020

(54) BIPHENYL SULFONAMIDE COMPOUNDS FOR THE TREATMENT OF KIDNEY DISEASES OR DISORDERS

(71) Applicant: Retrophin, Inc., San Diego, CA (US)

(72) Inventors: Radko Komers, Portland, OR (US); Alvin Shih, Newton, MA (US)

(73) Assignee: RETROPHIN, INC., San Diego, CA (US)

(*) Notice: Subject to any disclaimer, the term of this patent is extended or adjusted under 35 U.S.C. 154(b) by 0 days.

(21) Appl. No.: 16/882,206

(22) Filed: May 22, 2020

(65) Prior Publication Data

US 2020/0281901 A1    Sep. 10, 2020

Related U.S. Application Data

(63) Continuation of application No. 16/340,848, filed as application No. PCT/US2017/056538 on Oct. 13, 2017.

(Continued)

(51) Int. Cl.
| | |
|---|---|
| *A61K 31/42* | (2006.01) |
| *A61K 31/422* | (2006.01) |
| *A61P 13/12* | (2006.01) |

(52) U.S. Cl.
CPC ............ *A61K 31/422* (2013.01); *A61P 13/12* (2018.01)

(58) Field of Classification Search
CPC .................................................... A61K 31/422
(Continued)

(56) References Cited

U.S. PATENT DOCUMENTS

| | | | |
|---|---|---|---|
| 6,638,937 | B2 | 10/2003 | Murugesan et al. |
| 6,835,741 | B2 | 12/2004 | Murugesan et al. |

(Continued)

FOREIGN PATENT DOCUMENTS

| | | |
|---|---|---|
| CN | 1308536 A | 8/2001 |
| JP | 2003-520785 A | 7/2003 |

(Continued)

OTHER PUBLICATIONS

Miner et al. "The 2014 international workshop on Alport Syndrome," Kidney International, 2014, vol. 86, pp. 679-684 (Year: 2014).*

(Continued)

*Primary Examiner* — Shengjun Wang
(74) *Attorney, Agent, or Firm* — Seed Intellectual Property Law Group LLP

(57) ABSTRACT

Methods of treatment comprising administering a compound having structure (I), (Continued)

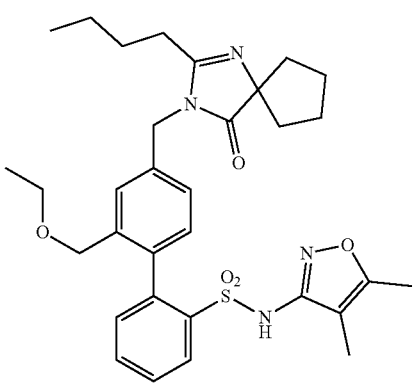

or a pharmaceutically acceptable salt thereof, or administering a pharmaceutical composition comprising the compound of structure (I) or pharmaceutically acceptable salt thereof, are provided.

18 Claims, 10 Drawing Sheets

Related U.S. Application Data

(60) Provisional application No. 62/423,079, filed on Nov. 16, 2016, provisional application No. 62/407,860, filed on Oct. 13, 2016.

(58) Field of Classification Search
USPC .......................................................... 514/378
See application file for complete search history.

(56) References Cited

U.S. PATENT DOCUMENTS

| | | | |
|---|---|---|---|
| 9,662,312 | B2 | 5/2017 | Zhang et al. |
| 9,993,461 | B2 | 6/2018 | Zhang et al. |
| 2002/0143024 | A1 | 10/2002 | Murugesan et al. |
| 2004/0106833 | A1 | 6/2004 | San et al. |
| 2015/0164865 | A1 | 6/2015 | Zhang et al. |
| 2015/0175695 | A1* | 6/2015 | Cosgrove ........... A61K 31/5377 424/172.1 |
| 2018/0344705 | A1 | 12/2018 | Zhang et al. |
| 2020/0147050 | A1 | 5/2020 | Komers et al. |

FOREIGN PATENT DOCUMENTS

| | | |
|---|---|---|
| WO | 00/01389 A1 | 1/2000 |
| WO | 01/44239 A2 | 6/2001 |
| WO | 2010/114801 A1 | 10/2010 |
| WO | 2010/135350 A2 | 11/2010 |

OTHER PUBLICATIONS

Adler et al., "Glomerular type IV collagen in patients with diabetic nephropathy with and without additional glomerular disease," *Kidney International* 57:2084-2092, 2000.
Barton, "Therapeutic potential of endothelin receptor antagonists for chronic proteinuric renal disease in humans," *Biochimica et Biophysica Acta* 1802: 1203-1213, 2010.
Barton et al., "Endothelin and the podocyte," *Clin Kidney J. 5*: 17-27, 2012.
Cameron, "Focal segmental glomerulosclerosis in adults," *Nephrol. Dial. Transplant.18* [Suppl 6]: vi45—vi51, 2003.
D'Agati et al., "Focal Segmental Glomerulosclerosis," *The New England Journal of Medicine 365*(25): 2398-2411, Dec. 22, 2011.
Delimont et al., "Laminin α2-Mediated Focal Adhesion Kinase Activation Triggers Alport Glomerular Pathogenesis," *PLOS One, Podocyte FAK Activation in Alport Syndrome 9*(6): e99083, 2014 (14 pages).
Dhaun et al., "Blood Pressure-Independent Reduction in Proteinuria and Arterial Stiffness After Acute Endothelin-A Receptor Antagonism in Chronic Kidney Disease," *Hypertension* 54: 113-119, 2009.
Dhaun et al., "Selective Endothelin-A Receptor Antagonism Reduces Proteinuria, Blood Pressure, and Arterial Stiffness in Chronic Proteinuric Kidney Disease," *Hypertension*: 772-779, Apr. 2011.
Doi, "Diagnosis and Treatment of Diabetic Nephropathy—The Current Status of Management and Its Problem," *The Journal of the Japanese Society of internal Medicine 96*(3):453-458,2007. (w/ English Abstract).
Duet Study "The effects of FSGS are more than just physical," Internet http://www.fsgsduetstudy.com/#p. 1, Retrieved Oct. 4, 2016 (4 pages).
Dufek et al., "Endothelin A receptor activation on mesangial cells initiates Alport glomerular disease," *Kidney International* 90: 300-310, 2016.
Fervenza et al., "Idiopathic Membranous Nephropathy: Diagnosis and Treatment," *Clin. J. Am. Soc. Nephrol. 3*: 905-919, 2008.
Gipson et al., "Clinical Trial of Focal Segmental Glomerulosclerosis in Children and Young Adults," *Kidney International 80*: 868-878, 2011.
González-Albarrädsn et al., "Role of Systolic Blood Pressure on the Progression of Kidney Damage in an Experimental Model of Type 2 Diabetes Mellitus, Obesity, and Hypertension (Zucker Rats)," AJH, 2003, vol. 16, No. 11, p. 979-985.
Gross et al., "Preemptive ramipril therapy delays renal failure and reduces renal fibrosis in COL4A3-knockout mice with Alport syndrome[1] ," *Kidney International 63*:438-446, 2003.
Ikeda et al., "Next generation ARBs: Going Beyond Modulation of the Renin-Angiotensin System," *Int. Heart J.* 585-586, 2015.
Inker et al., "Early Change in Urine Protein as a Surrogate End Point in Studies of IgA Nephropathy: An Individual-Patient Meta-analysis," *Am. J. Kidney Dis. 68*(3): 392-401, 2016.
Inker et al., "Early Change in Urine Protein as a Surrogate End Point in Studies of IgA Nephropathy: An Individual-Patient Meta-analysis," *Am. J. Kidney Dis. 68*(3): 392-401, 2016, Supplemental Pages (12 pages).
Jaipaul, "Diabetic Nephropathy," Merck Manual Professional Version, pp. 1-5, 2018.
Kangovi et al., "Renin-Angiotensin-aldosterone system inhibitors in pediatric focal segmental glomerulosclerosis," *Pediatr Nephrol,* 2011 (7 pages).
Kiffel et al. "Focal Segmental Glomerulosclerosis and Chronic Kidney Disease in Pediatric Patients," *Adv. Chronic Kidney Dis. 18*(5):332-338, 2011.
Kitiyakara et al., "Twenty-One-Year Trend in ESRD Due to Focal Segmental Glomerulosclerosis in the United States," *American Journal of Kidney Diseases* vol. 44, No. 5 (Nov.): 815-825, 2004.
Kohan et al., "Addition of Atrasentan to Renin-Angiotensin System Blockade Reduces Albuminuria in Diabetic Nephropathy," *J. Am. Soc. Nephrol. 22*(4): 763-772, 2011.
Kohan et al., "Endothelin and Endothelin Antagonists in Chronic Kidney Disease," *Kidney International 86*:896-904, 2014.
Komers et al., "Dual inhibition of renin-angiotensin-aldosterone system and endothelin-1 in treatment of chronic kidney disease," *Am. J. Physiol. Regul. Integr. Comp. Physiol.* 310:R877-R884, 2016.
Komers et al., "Efficacy and Safety of Sparsentan Compared With Irbesartan in Patients With Primary Focal Segmental Glomerulosclerosis: Randomized, Controlled Trial Design (DUET)," *Kidney International Reports* 2:654-664, 2017.
Kowala et al., "Novel Dual Action $AT_1$ and $ET_A$ Receptor Antagonists Reduce Blood Pressure in Experimental Hypertension," *The Journal of Pharmacology and Experimental Therapeutics 309*(1):275-284, 2004.
Mann et al., "Avosentan for Overt Diabetic Nephropathy," *J. Am. Soc. Nephrol.* 21: 527-535, 2010.

(56) References Cited

OTHER PUBLICATIONS

Meehan et al., "Endothelin-1 mediated induction of extracellular matrix genes in strial marginal cells underlies strial pathology in Alport mice," *Hearing Research 341*:100-108, 2016.

Murugesan et al., "Dual Angiotensin II and Endothelin A Receptor Antagonists: Synthesis of 2'Substituted N-3- lsoxazolyl Biphenylsulfonamides with Improved Potency and Pharmacokinetics," *J. Med. Chem. 48*: 171-179, 2005.

Neutel et al., "Abstract 4420: Results of a Double Blind Placebo Controlled Study to Evaluate the Efficacy and Safety of PS433540 in Human Subjects with Hypertension," *Circulation 118*:S_886, 2008, 1 page.

Neutel et al., "Results of a double blind, placebo controlled study to evaluating PS433540, a novel dual acting receptor antagonist in stage I and II hypertenives," *J. Am. Soc. Nephrol. 19* 2008, 2 pages.

New Drug Approvals "Sparsentan (PS433540,RE-021)," retrieved from https://newdrugapprovals.org/2015/10/12/sparsentan-ps433540-re-021/ on Dec. 17, 2019 (10 pages).

O'Riordan, "Dual-acting receptor antagonist reduces systolic blood pressure: No safety signals raised in phase 2a trial," *Heartwire*, May 19, 2008, retrieved from https://www.medscape.com/viewarticle/574699, on Aug. 28, 2019, 2 pages.

Pharmacopeia, "Investor Presentation PS433540 Phase 2a Study Results," May 16, 2008, retrieved from http://www.sec.gov/Archives/edgar/data/1273013/000110465908033876/a08-14253 2ex99d2.htm, 12 pages.

Praga et al., "Treatment of IgA Nephropathy with ACE Inhibitors: A Randomized and Controlled Trial," *J. Am. Soc. Nephrol. 14*: 1578-1583, 2003.

Reich et al., "Remission of Proteinuria Improves Prognosis in IgA Nephropathy," *J. Am. Soc. Nevhrol.18*: 3177-3183, 2007.

Retrophin, Inc., "Randomized, Double-Blind, Safety and Efficacy Study of RE-021 (Sparsentan) in Focal Segmental Glomerulosclerosis (DUET)," ClinicalTrials.gov, ClinicalTrials.gov Identifier: NCT01613118, 2012 (3 pages).

Retrophin, Inc., "Retrophin Announces Positive Top-Line Results from Phase 2 DUET Study of Sparsentan in Patients with Focal Segmental Glomerulosclerosis," Press Release, Sep. 7, 2016, 3 pages.

Ritz et al., "Endothelin Antagonist as Add-on Treatment for Proteinuria in Diabetic Nephropathy: Is There Light at the End of the Tunnel?" *J. Am. Soc. Nephrol. 22*: 593-595, 2011.

Schieppati et al., "Prognosis of Untreated patients with Idiopathic Membranous Nephropathy," *The New England Journal of Medicine 329*(2):85-89, 1993.

Shacter et al., "Chronic Inflammation and Cancer," *Cancer Network 16*(2): 1-8, 2002.

Thompson Pharma Integrity, Entry 307300 for Drug Name "PS433540," Retrieved Jun. 8, 2013, 2 pages.

Tobe et al., "Endothelin Receptor Antagonists: New Hope for Renal Protection?" *Curr. Hypertens Rep. 17*: 57, 2015 (7 pages).

Trachtman, "Investigational drugs in development for focal segmental glomerulosclerosis," *Expert Opinion on Investigational Drugs 26*(8):945-952, 2017.

Van der Loop et al., "Autosomal dominant Alport syndrome caused by a COL4A3 splice site mutation," *Kidney International 58*:1870-1875, 2000.

Wenzel et al., "Avosentan Reduces Albumin Excretion in Diabetics with Macroalbuminuria," *J. Am. Soc. Nephrol.20*: 655-664, 2009.

Yuzawa, "Pathophysiology, Diagnosis and Treatment of Primary Nephrotic Syndrome," *The Journal of the Japanese Society of internal Medicine*, 2009, vol. 98, No. 5, p. 1016-1022, with English abstract.

Cosgrove et al., "The Dual Endothelin/Angiotensin II Receptor ($ET_4R/AT_1R$) Antagonist Sparsentan Slows Renal Disease, Improves Lifespan, and Attenuates Hearing Loss in Alport Mice: Comparison with Losartan and Atrasentan," Presented at the German Society of Nephrology 12th Annual Virtual Congress 2020, Oct. 1-4, 2020 (1 Page).

Kashtan et al., "Alport syndrome: a unified classification of genetic disorders of collagen IV α345: a position paper of the Alport Syndrome Classification Working Group," *Kidney International 93*:1045-1051, 2018.

* cited by examiner

BIPHENYL SULFONAMIDE COMPOUNDS FOR THE TREATMENT OF KIDNEY DISEASES OR DISORDERS

BACKGROUND

Technical Field

The present disclosure relates to the use of biphenyl sulfonamide compounds that are dual angiotensin and endothelin receptor antagonists in the treatment of kidney diseases or disorders, such as focal segmental glomerulosclerosis (FSGS).

Description of the Related Art

Angiotensin II (AngII) and endothelin-I (ET-1) are two of the most potent endogenous vasoactive peptides currently known and are believed to play a role in controlling both vascular tone and pathological tissue remodeling associated with a variety of diseases including diabetic nephropathy, heart failure, and chronic or persistently elevated blood pressure. Angiotensin receptor blockers (ARBs), which block the activity of AngII, have been used as a treatment for diabetic nephropathy, heart failure, chronic, or persistently elevated blood pressure. In addition, there is a growing body of data that demonstrates the potential therapeutic benefits of ET receptor antagonists (ERAs) in blocking ET-1 activity.

AngII and ET-1 are believed to work together in blood pressure control and pathological tissue remodeling. For example, ARBs not only block the action of AngII at its receptor, but also limit the production of ET-1. Similarly, ERAs block ET-1 activity and inhibit the production of AngII. Consequently, simultaneously blocking AngII and ET-1 activities may offer better efficacy than blocking either substance alone.

In rat models of human chronic or persistently elevated blood pressure, the combination of an ARB and an ERA has been shown to result in a synergistic effect. Furthermore, although ARBs are the standard of care for patients with diabetic nephropathy, improved efficacy with the co-administration of an ERA has been reported in Phase 2 clinical development.

Focal segmental glomerulosclerosis (FSGS) is a rare disease that affects the kidneys. Patients with FSGS exhibit scarring of the glomeruli of the kidney. Glomeruli filter the blood and remove water and some toxins, producing urine and leaving proteins behind in the blood. The scarring of the glomeruli in patients with FSGS is associated with leakage of protein into the urine (instead of remaining in the blood), a condition called proteinuria. Proteinuria causes fluid to build up in the body. Additionally, protracted proteinuria may result in damage to the kidneys and kidney dysfunction. FSGS is categorized as primary (or "idiopathic"), secondary, or genetic. Primary FSGS has no known etiology. Secondary FSGS may be caused by reduction in renal mass, including that which may be associated with low birth weight; vesicoureteral reflux; obesity; medications; infections, including HIV infection; or systemic illnesses, such as diabetes, sickle cell anemia, and lupus. There is currently no approved treatment for FSGS. If FSGS goes untreated, it can lead to end-stage renal disease (ESRD) over five to ten years.

In addition to FSGS, other kidney diseases or disorders characterized by damage to the glomeruli include IgA nephropathy and idiopathic membranous nephropathy. IgA nephropathy, also known as Berger's disease, is caused by the buildup of immunoglobulin A (IgA) in the kidney. The presence of IgA in the kidneys may lead to inflammation, damage to the glomeruli of the kidney, and impaired kidney function, including proteinuria. In some cases, patients with IgA nephropathy progress to ESRD.

Idiopathic membranous nephropathy (IMN) is characterized by inflammation and thickening of glomeruli of the kidney, and is the most common glomerular disease associated with nephrotic syndrome. Similar to FSGS and IgA nephropathy, IMN is also characterized by proteinuria and, in some patients, may also advance to ESRD (see Schieppati et al., *N. Engl. J. Med.* 329(2): 85-89, 1993).

For kidney diseases characterized by proteinuria, a reduction in proteinuria may be associated with improved outcome. For example, complete or partial remission in proteinuria has been correlated with long-term positive outcomes in patients with IMN (Schieppati et al., 1993; Fervenza et al., *Clin. J. Am. Soc. Nephrol.* 3: 905-919, 2008). Current methods used to decrease proteinuria include the administration of steroids or medications that lower high blood pressure, lower high cholesterol, remove the extra fluid from the body, or suppress the immune system. For example, FSGS patients may be treated with steroids, calcineurin inhibitors, angiotensin receptor blockers (ARB), and angiotensin converting inhibitors (ACE) to lower proteinuria (see, e.g., Cameron, *Nephrol. Dial. Transplant.* 18 (Suppl. 6): vi45-vi51, 2003), but such therapies are often ineffective in reducing proteinuria (Kiffel et al., *Adv. Chronic Kidney Dis.* 18(5): 332-338, 2011). Endothelin receptor antagonists (ERA) have been shown to lower proteinuria in clinical trials of diabetic nephropathy (Mann et al., *J. Am. Soc. Nephrol.* 21(3): 527-535, 2010; Kohan et al., *J. Am. Soc. Nephrol.* 22(4): 763-772, 2011) and have been speculated to be effective in FSGS (Barton, *Biochimica et Biophysica Acta* 1802: 1203-1213, 2010).

Thus, there remains a need for compositions and methods for treating various kidney diseases or disorders, such as FSGS, IgA nephropathy, and IMN.

BRIEF SUMMARY

In some embodiments, the present invention is directed to pharmaceutical compositions comprising a compound having structure (I),

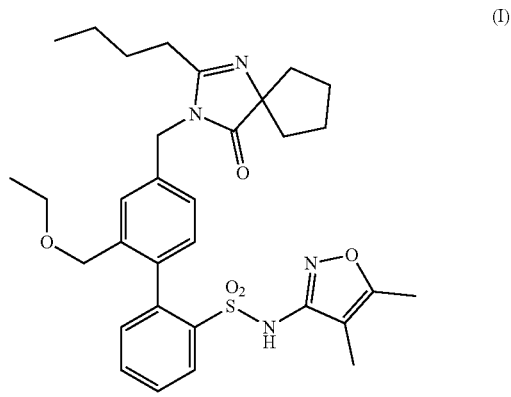 [SMILES: CCCCC1=NC2(CCCC2)C(=O)N1Cc1ccc(-c2ccccc2S(=O)(=O)Nc2noc(C)c2C)c(COCC)c1]

or a pharmaceutically acceptable salt thereof, for use in methods of treating a kidney disease or disorder in a subject in need thereof, the methods comprising administering to said subject said pharmaceutical composition (i) in an amount sufficient to achieve a urine protein to creatinine ("UP/C") ratio of less than or equal to 1.5 g/g; (ii) in an amount sufficient to achieve or maintain a UP/C ratio of less than or equal to 1.5 g/g; or (iii) at a dosing regimen sufficient to achieve or maintain a UP/C ratio of less than or equal to 1.5 g/g.

In some embodiments, the present invention is directed to pharmaceutical compositions comprising a compound having structure (I), or a pharmaceutically acceptable salt thereof, for use in therapeutic methods of (i) maintaining a UP/C ratio at less than or equal to 1.5 g/g in a subject in need thereof, the method comprising administering to said subject said pharmaceutical composition in an amount sufficient to maintain a UP/C ratio of less than or equal to 1.5 g/g; or (ii) reducing a UP/C ratio to less than or equal to 1.5 g/g in a subject in need thereof, the method comprising administering to said subject said pharmaceutical composition in an amount sufficient to reduce said patient's UP/C ratio to less than or equal to 1.5 g/g. In some embodiments, the present invention is directed to methods of treating a kidney disease or disorder in a subject in need thereof, the methods comprising administering to the subject a pharmaceutical composition comprising a compound having structure (I),

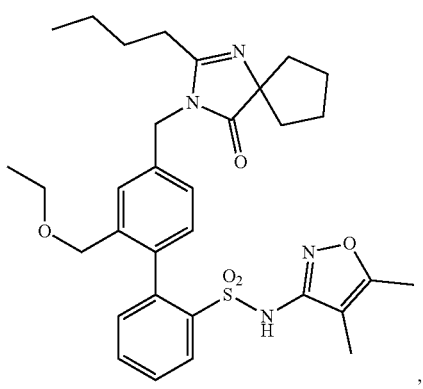
(I)

or a pharmaceutically acceptable salt thereof, in an amount sufficient to achieve a urine protein to creatinine (UP/C) ratio of less than or equal to 1.5 g/g.

In some further embodiments, methods of treating a kidney disease or disorder in a subject in need thereof are provided, the methods comprising administering to the subject a pharmaceutical composition comprising a compound having structure (I), or a pharmaceutically acceptable salt thereof, in an amount sufficient to achieve or maintain a UP/C ratio of less than or equal to 1.5 g/g.

In some further embodiments, the present invention is directed to methods of treating a kidney disease or disorder in a subject in need thereof, the methods comprising administering to the subject a pharmaceutical composition comprising a compound having structure (I), or a pharmaceutically acceptable salt thereof, at a dosing regimen sufficient to achieve or maintain a UP/C ratio of less than or equal to 1.5 g/g.

In some further embodiments, the present invention is directed to methods of treating a kidney disease or disorder in a subject in need thereof, the methods comprising administering to the subject, over an administration period, a pharmaceutical composition comprising a compound having structure (I), or a pharmaceutically acceptable salt thereof, in an amount sufficient to achieve or maintain a UP/C ratio of less than or equal to 1.5 g/g for at least a portion of the administration period.

In some further embodiments, the present invention is directed to methods of maintaining a UP/C ratio at less than or equal to 1.5 g/g in a subject in need thereof, the methods comprising administering to the subject a pharmaceutical composition comprising a compound having structure (I), or a pharmaceutically acceptable salt thereof, in an amount sufficient to maintain a UP/C ratio of less than or equal to 1.5 g/g.

In some further embodiments, the present invention is directed to methods of reducing a UP/C ratio to less than or equal to 1.5 g/g in a subject in need thereof, comprising administering to the subject a pharmaceutical composition comprising a compound having structure (I), or a pharmaceutically acceptable salt thereof, in an amount sufficient to reduce said patient's UP/C ratio to less than or equal to 1.5 g/g.

These and other aspects of the present invention will become apparent upon reference to the following detailed description. All references disclosed herein are hereby incorporated by reference in their entirety as if each was incorporated individually.

DETAILED DESCRIPTION

Figure 1A:
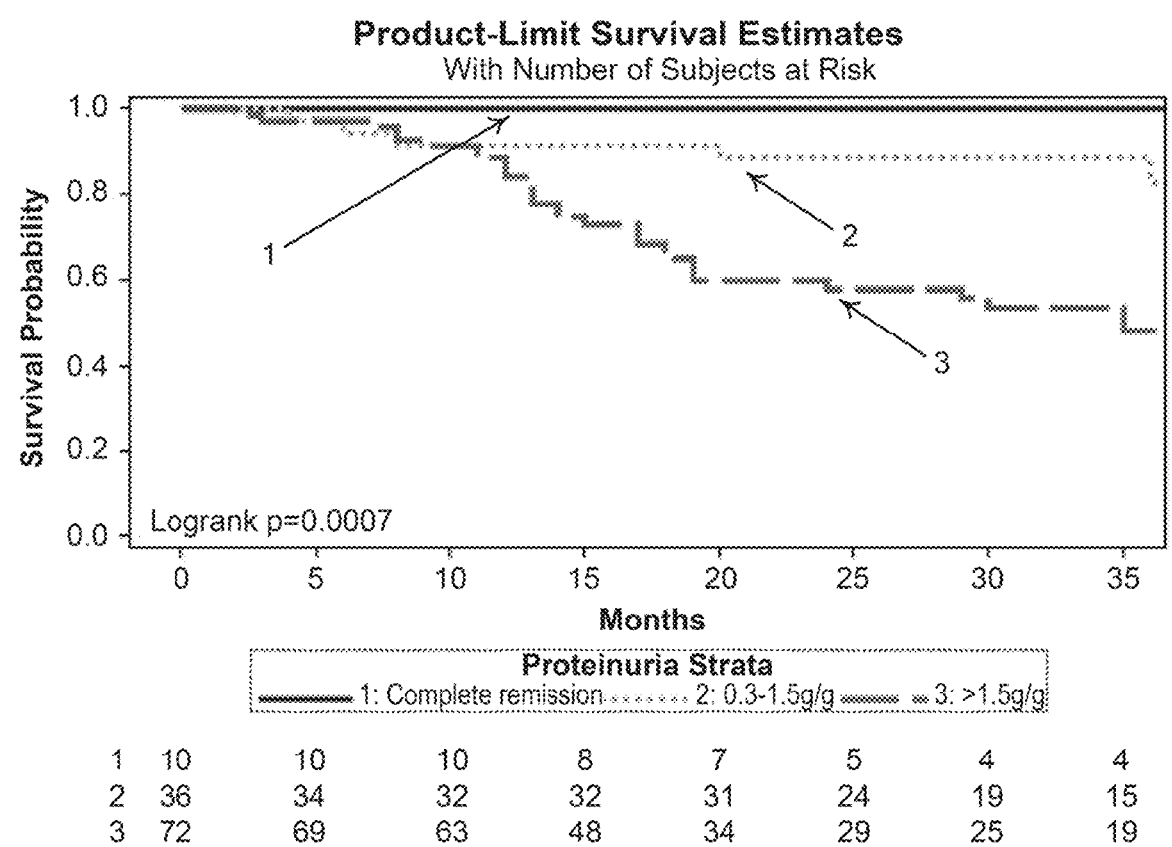
FIG. 1A. Proteinuria Strata and Progression to Subsequent End-Stage Renal Disease (ESRD) or 40% Reduction in Estimated Glomerular Filtration Rate (eGFR) for NEPTUNE data (n=118). They-axis shows survival probability for patients showing complete remission (UP/C ratio less than 0.3 g/g; proteinuria strata "1"), proteinuria levels of 0.3 to 1.5 g/g (proteinuria strata "2"), or proteinuria levels of greater than 1.5 g/g (proteinuria strata "3"). The x-axis shows time in months.

The present disclosure generally relates to the use of biphenyl sulfonamide compounds that are dual angiotensin and endothelin receptor antagonists in the treatment of kidney diseases or disorders, such as focal segmental glomerulosclerosis (FSGS), IgA nephropathy, and idiopathic membranous nephropathy (IMN).

In the following description, certain specific details are set forth in order to provide a thorough understanding of various embodiments of the invention. However, one skilled in the art will understand that the invention may be practiced without these details.

Unless defined otherwise, all technical and scientific terms used herein have the same meaning as is commonly understood by one of skill in the art to which this invention belongs. As used herein, certain terms may have the following defined meanings.

Unless the context requires otherwise, throughout the present specification and claims, the word "comprise" and variations thereof, such as "comprises" and "comprising," are to be construed in an open, inclusive sense, that is, as "including, but not limited to."

As used in the specification and claims, "including" and variants thereof, such as "include" and "includes," are to be construed in an open, inclusive sense; i.e., it is equivalent to "including, but not limited to." As used herein, the terms "include" and "have" are used synonymously, which terms and variants thereof are intended to be construed as non-limiting.

As used in herein, the phrase "such as" refers to non-limiting examples.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in the specification and claims, the singular for "a," "an," and "the" include plural references unless the context clearly dictates otherwise. For example, the term "a cell" includes a plurality of cells, including mixtures thereof. Similarly, use of "a compound" for treatment of preparation of medicaments as described herein contemplates using one or more compounds of the invention for such treatment or preparation unless the context clearly dictates otherwise.

The use of the alternative (e.g., "or") should be understood to mean either one, both, or any combination thereof of the alternatives.

"Optional" or "optionally" means that the subsequently described event of circumstances may or may not occur, and that the description includes instances where said event or circumstance occurs and instances in which it does not occur.

As used herein, "about" and "approximately" generally refer to an acceptable degree of error for the quantity measured, given the nature or precision of the measurements. Typical, exemplary degrees of error may be within 20%, 10%, or 5% of a given value or range of values. Alternatively, and particularly in biological systems, the terms "about" and "approximately" may mean values that are within an order of magnitude, potentially within 5-fold or 2-fold of a given value. When not explicitly stated, the terms "about" and "approximately" mean equal to a value, or within 20% of that value.

As used herein, numerical quantities are precise to the degree reflected in the number of significant figures reported. For example, a value of 0.1 is understood to mean from 0.05 to 0.14. As another example, the interval of values 0.1 to 0.2 includes the range from 0.05 to 0.24.

The compound having structure (I) forms salts that are also within the scope of this disclosure. Reference to a compound having structure (I) herein is understood to include reference to salts thereof, unless otherwise indicated. The term "salt(s)," as employed herein, denotes acidic, or basic salts formed with inorganic or organic acids and bases. In addition, as the compound having structure (I) contains both a basic moiety and an acidic moiety, zwitterions ("inner salts") may be formed and are included within the term "salt(s)," as used herein. Pharmaceutically acceptable (i.e., non-toxic, physiologically acceptable) salts are preferred, although other salts may be useful, e.g., in isolation or purification steps which may be employed during preparation. Salts of the compound having structure (I) may be formed, for example, by reacting the compound having structure (I) with an amount of acid or base, such as an equivalent amount, in a medium such as one in which the salt precipitates or in an aqueous medium followed by lyophilization.

The term "pharmaceutically acceptable salt" includes both acid and base addition salts.

Prodrugs and solvates of the compound having structure (I) are also contemplated. The term "prodrug" denotes a compound which, upon administration to a subject, undergoes chemical conversion by metabolic or chemical processes to yield a compound having structure (I), or a salt or solvate thereof. Solvates of the compound having structure (I) may be hydrates. Any tautomers are also contemplated.

Often crystallizations produce a solvate of the compound having structure (I), or a salt thereof. As used herein, the term "solvate" refers to an aggregate that comprises one or more molecules of a compound as disclosed herein with one or more molecules of solvent. In some embodiments, the solvent is water, in which case the solvate is a hydrate. Alternatively, in other embodiments, the solvent is an organic solvent. Thus, the compounds of the present disclosure may exist as a hydrate, including a monohydrate, dihydrate, hemihydrate, sesquihydrate, trihydrate, tetrahydrate, and the like, as well as the corresponding solvated forms. In some embodiments, the compounds disclosed herein may be a true solvate, while in other cases, the compounds disclosed herein merely retain adventitious water or are mixtures of water plus some adventitious solvent.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabeled compound of the invention in a detectable dose to an animal, such as rat, mouse, guinea pig, monkey, or to human, allowing sufficient time for metabolism to occur, and isolating its conversion products from the urine, blood, or other biological samples.

"Stable compound" and "stable structure" are meant to indicate a compound that is sufficiently robust to survive isolation to a useful degree of purity from a reaction mixture, and formulation into an efficacious therapeutic agent.

The term "subject" refers to a mammal, such as a domestic pet (for example, a dog or cat), or human. Preferably, the subject is a human.

The phrase "effective amount" refers to the amount which, when administered to a subject or patient for treating a disease, is sufficient to effect such treatment for the disease.

The term "dosage unit form" is the form of a pharmaceutical product, including, but not limited to, the form in which the pharmaceutical product is marketed for use. Examples include pills, tablets, capsules, and liquid solutions and suspensions.

"Treatment" or "treating" includes (1) inhibiting a disease in a subject or patient experiencing or displaying the pathology or symptomatology of the disease (e.g., arresting further development of the pathology or symptomatology); or (2) ameliorating a disease in a subject or patient that is experiencing or displaying the pathology or symptomatology of the disease (e.g., reversing the pathology or symptomatology); or (3) effecting any measurable decrease in a disease in a subject or patient that is experiencing or displaying the pathology or symptomatology of the disease.

Additional definitions are set forth throughout this disclosure.

Chemical Compounds and Methods of Preparation

The present disclosure generally relates to the use of biphenyl sulfonamide compounds that are dual angiotensin and endothelin receptor antagonists. In particular, the present disclosure relates to biphenyl sulfonamide compounds such as a compound having structure (I),

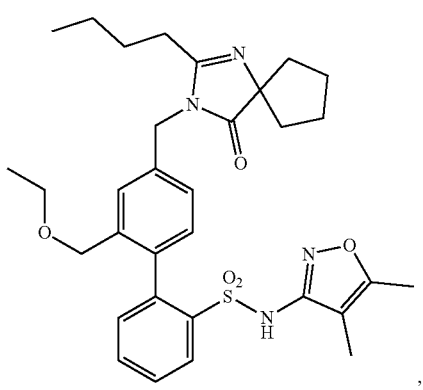

(I)

and pharmaceutically acceptable salts thereof. The compound of structure (I) is also known as sparsentan. The compound of structure (I) is a selective dual-acting receptor antagonist with affinity for endothelin (A type) receptors ("ET$_A$" receptors) and angiotensin II receptors (Type 1) ("AT$_1$" receptors) (Kowala et al., *JPET* 309: 275-284, 2004).

The compound of structure (I) may be prepared by methods such as those illustrated in the following Scheme I. Solvents, temperatures, pressures, and other reaction conditions may be selected by one of ordinary skill in the art.

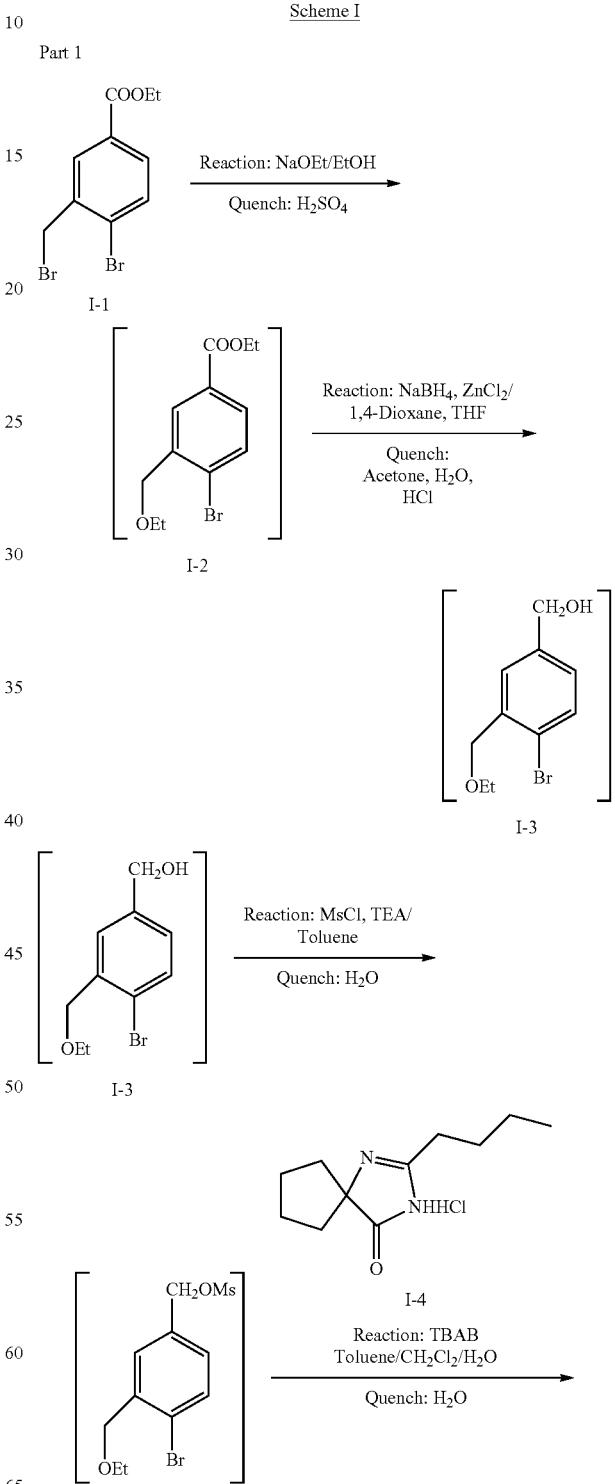

Scheme I

-continued
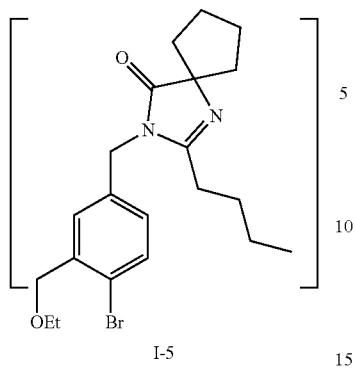
I-5
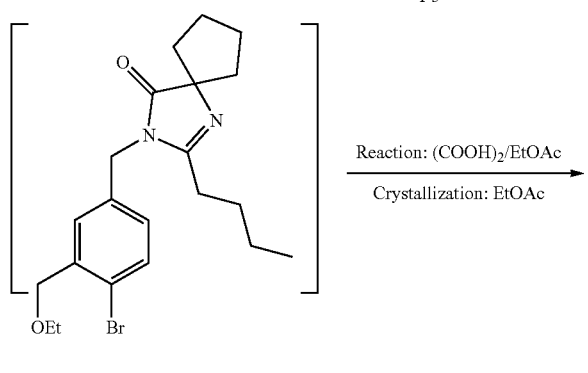
I-6
Part 2
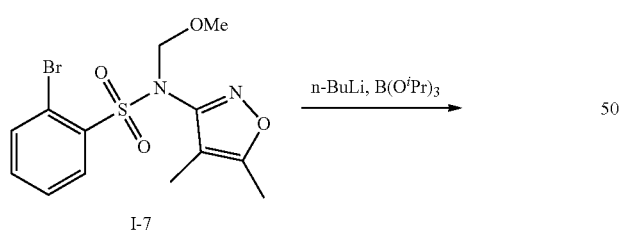
I-7
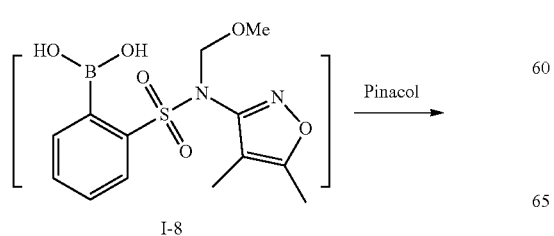
I-8
-continued
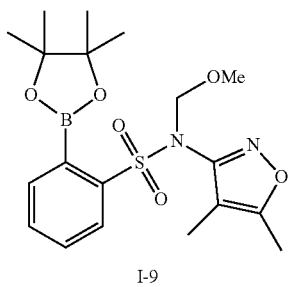
I-9
Part 3
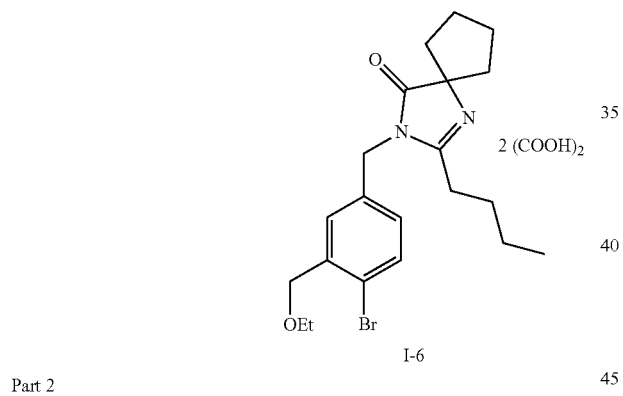
I-7
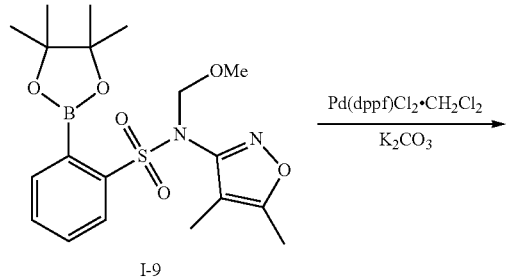
I-9
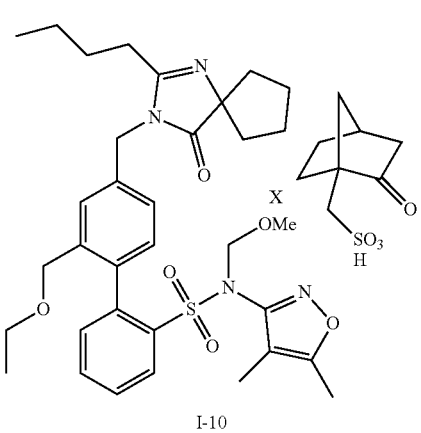
I-10

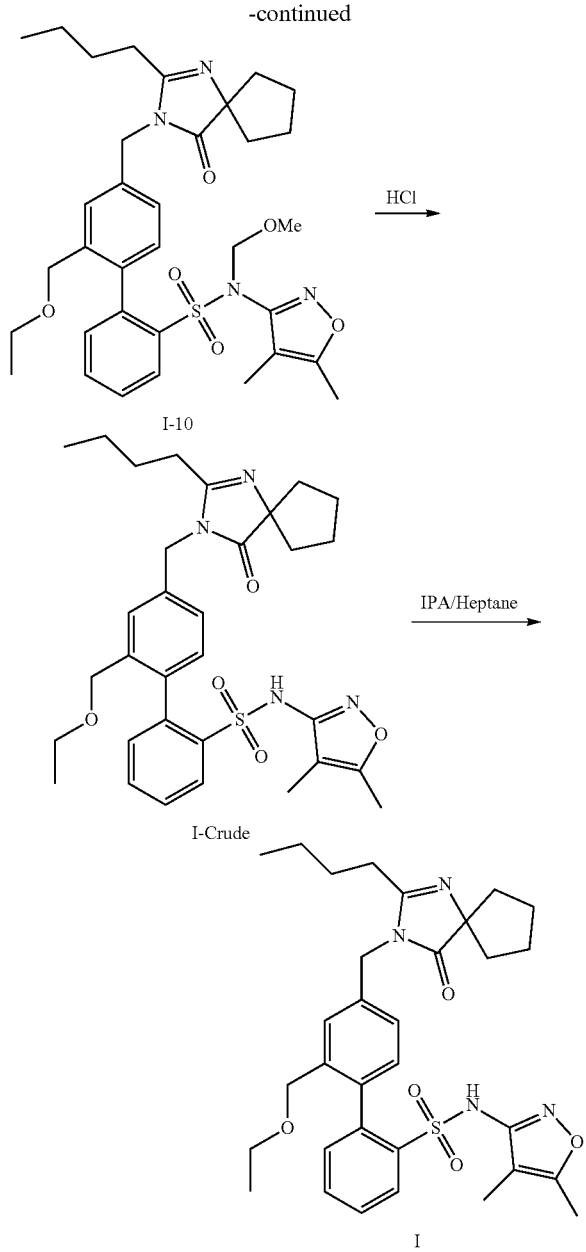

Part 1: Ethyl-4-bromo-3-(bromomethyl)benzoate (I-1) can be treated with sodium ethoxide in ethanol to provide ethyl-4-bromo-3-(ethoxymethyl)benzoate (I-2). Ethyl-4-bromo-3-(ethoxymethyl)benzoate can be converted to (4-bromo-3-(ethoxymethyl)phenyl)methanol (I-3) with the additions of sodium borohydride and zinc chloride in 1,4-dioxane/THF. (4-bromo-3-(ethoxymethyl)phenyl)methanol is converted to the benzyl methanesulfonate with methylsulfonyl chloride, followed by coupling to 2-Butyl-1,3-diazaspiro[4,4]non-1-en-4-one hydrochloride (I-4) in the presence of tetrabutylammonium bromide to form 3-(4-bromo-3(ethoxymethyl)benzyl)-2-Butyl-1,3-diazaspiro[4,4]non-1-en-4-one (I-5). The penultimate intermediate is isolated by crystallization to form 3-(4-bromo-3(ethoxymethyl)benzyl)-2-Butyl-1,3-diazaspiro[4,4]non-1-en-4-one oxalic acid (I-6).

Part 2: 2-bromo-N-(4,5-dimethylisoxazol-3yl)-N-(methoxymethyl)benzenesulfonamide (I-7) is reacted with triisopropyl borate/n-butyl lithium/tetrahydrofuran to form (2-(N-(4,5-dimethylisoxazol-3yl)-N-(methoxymethyl)sulfamoyl)phenyl)boronic acid (I-8). (2-(N-(4,5-dimethylisoxazol-3yl)-N-(methoxymethyl)sulfamoyl)phenyl)boronic acid reacted with pinacol yields penultimate intermediate-2, N-(4,5-dimethylisoxazol-3yl)-N-(methoxymethyl)-2-(4,4,5,5-tetramethyl-1,3,2-diozaborolan-2-yl)benzenesulfonamide (I-9).

Part 3: Under nitrogen, I-7 is suspended in toluene/potassium carbonate solution. The aqueous phase is removed. To the solvent phase add I-9, potassium carbonate solution, and 1,1'-bis(diphenylphosphino)ferrocene-palladium(II)dichloride dichloromethane complex. The reaction mixture is heated and mixed. The solvent phase is removed and charged with trithiocyanuric acid and activated charcoal. The reaction mixture is stirred at temperature and then cooled. The carbon is then filtered and washed repeatedly with toluene. The combined filtrates are concentrated by distillation and charged with isopropyl alcohol (IPA). Toluene is removed from the solution through repeated distillations and additions of IPA. Camphor sulfonic acid, n-heptane, and seed crystals are charged to the solution. The resulting suspension is filtered and dried to isolate 4'-((2-butyl-4-oxo-1,3-diazaspiro[4.4]non-1-en-3-yl)methyl)-N-(4,5-dimethylisoxazol-3-yl)-2'-(ethoxymethyl)-N-(methoxymethyl)-[1,1'-biphenyl]-2sulfonamide camphor sulfonic acid (I-10). I-10 is then treated with concentrated hydrochloric acid in ethanol/water at temperature to remove the methoxymethyl protecting group resulting in the crude product (I-Crude). The crude product (I-Crude) is then purified and isolated by crystallization with isopropyl alcohol and n-heptanes to provide the compound of formula I, 4'-((2-butyl-4-oxo-1,3-diazaspiro[4.4]non-1-en-3-yl)methyl)-N-(4,5-dimethylisoxazol-3-yl)-2'-(ethoxymethyl)-[1,1'-biphenyl]-2-sulfonamide.

Additionally, the compound of structure (I) may be prepared by the methods recited in U.S. Patent Application Publication No. US 2015/0164865 A1 and U.S. Pat. No. 6,638,937 B2.

Pharmaceutical Compositions and Methods of Use

In one embodiment, the present disclosure relates to the administration of a pharmaceutical composition comprising a compound of structure (I), or pharmaceutically acceptable salt thereof, and a pharmaceutically acceptable excipient. The term "pharmaceutical composition" as used herein refers to a composition comprising an active ingredient with a pharmaceutically acceptable excipient. Pharmaceutical compositions may be used to facilitate administration of an active ingredient to an organism. Multiple techniques of administering a compound exist in the art, such as oral, injection, aerosol, parenteral, and topical administration. Pharmaceutical compositions can be obtained, for example, by reacting compounds with inorganic or organic acids such as hydrochloric acid, hydrobromic acid, sulfuric acid, nitric acid, phosphoric acid, methane sulfonic acid, ethanesulfonic acid, p-toluenesulfonic acid, salicylic acid, and the like. As used herein, the term "physiologically acceptable excipient" refers to a physiologically and pharmaceutically suitable non-toxic and inactive material or ingredient that does not interfere with the activity of the active ingredient, including any adjuvant, carrier, glidant, sweetening agent, diluent, preservative, dye/colorant, flavor enhancer, surfactant, wetting agent, dispersing agent, suspending agent, stabilizer, isotonic agent, solvent, or emulsifier that has been approved by the United States Food and Drug Administration as being acceptable for use in humans or domestic animals. In some embodiments, the pharmaceutical composition may be formulated as described below. Additionally, methods of treating diseases or disorders by administering a pharmaceutical composition comprising a compound of structure (I), or pharmaceutically acceptable salt thereof, and a pharmaceutically acceptable excipient, are also within the scope of the present disclosure.

In one embodiment, the compound of structure (I) and pharmaceutically acceptable salts thereof are useful in the treatment of conditions associated with increased endothelin levels and/or increased AngII levels, and in treatment of endothelin-dependent or angiotensin II-dependent disorders. Accordingly, in a specific embodiment, a method of treating an endothelin-dependent or angiotensin II-dependent disorder is provided, comprising administering to a subject in need thereof a pharmaceutical composition comprising an effective amount of a compound of structure (I), or a pharmaceutically acceptable salt thereof.

In another embodiment, the compound of structure (I) and pharmaceutically acceptable salts thereof are useful in reducing proteinuria. As used herein, "proteinuria" refers to a condition in which the urine contains an abnormal amount of protein (i.e., urine protein excretion of greater than 300 mg per day). A urine protein to creatinine ("UP/C") ratio provides a measurement of total urine protein relative to the amount of creatinine in a urine sample (e.g., 1 g of protein in urine (dl) divided by 1 g of creatinine in urine (dl)=a UP/C ratio of 1). As used herein, a UP/C ratio of more than 0.3 g/g indicates proteinuria. In a particular embodiment, the compound of structure (I) and pharmaceutically acceptable salts thereof are useful in reducing proteinuria to levels to less than or equal to 1.5 g/g.

In one embodiment, the compound of structure (I) and pharmaceutically acceptable salts thereof are useful in the treatment of kidney diseases or disorders.

In a further embodiment, the compound of structure (I) and pharmaceutically acceptable salts thereof are useful in the treatment of disorders related to renal, glomerular, and mesangial cell function, including acute (such as ischemic, nephrotoxic, or glomerulonephritis) and chronic (such as diabetic, hypertensive, or immune-mediated) renal failure, diabetic nephropathy, glomerular injury, renal damage secondary to old age or related to dialysis, nephrosclerosis (especially hypertensive nephrosclerosis), nephrotoxicity (including nephrotoxicity related to imaging and contrast agents and to cyclosporine), renal ischemia, primary vesicoureteral reflux, glomerulosclerosis, and the like. In one embodiment, the compound of structure (I) and pharmaceutically acceptable salts thereof are useful in the treatment of disorders related to glomerular function.

In still another embodiment, the compound of structure (I) and pharmaceutically acceptable salts thereof are useful in the treatment of focal segmental glomerulosclerosis (FSGS). Accordingly, in a specific embodiment, a method of treating FSGS is provided, comprising administering to a subject in need thereof a pharmaceutical composition comprising an effective amount of a compound of structure (I), or a pharmaceutically acceptable salt thereof. In another embodiment, a method of treating primary (or idiopathic) FSGS, comprising administering to a subject in need thereof a pharmaceutical composition comprising an effective amount of a compound of structure (I), or a pharmaceutically acceptable salt thereof. In yet another embodiment, a method of treating secondary FSGS is provided, comprising administering to a subject in need thereof a pharmaceutical composition comprising an effective amount of a compound of structure (I), or a pharmaceutically acceptable salt thereof. The secondary FSGS may be associated with, for example, a reduction in renal mass, including that which may be associated with low birth weight; vesicoureteral reflux; obesity; a medication; an infection, including HIV infection; or a systemic illness such as diabetes, sickle cell anemia, or lupus. In yet another embodiment, a method of treating genetic FSGS is provided, comprising administering to a subject in need thereof a pharmaceutical composition comprising an effective amount of a compound of structure (I), or a pharmaceutically acceptable salt thereof. In any of these embodiments, the method of treating FSGS may comprise administering the pharmaceutical composition is an amount sufficient to reduce a UP/C ratio to less than or equal to 1.5 g/g.

In a further embodiment, the compound of structure (I) and pharmaceutically acceptable salts thereof are useful in the treatment of IgA nephropathy.

In a further embodiment, the compound of structure (I) and pharmaceutically acceptable salts thereof are useful in the treatment of idiopathic membranous nephropathy (IMN).

In a further embodiment, the compound of structure (I) and pharmaceutically acceptable salts thereof are useful in the treatment of diabetic nephropathy and hypertension-induced nephropathy. Accordingly, in a specific embodiment, a method of treating diabetic nephropathy or hypertension-induced nephropathy is provided, comprising administering to a subject in need thereof a pharmaceutical composition comprising an effective amount of a compound of structure (I), or a pharmaceutically acceptable salt thereof.

In a further embodiment, the compound of structure (I) and pharmaceutically acceptable salts thereof are useful in the treatment of Alport syndrome.

In a further embodiment, the compound of structure (I) and pharmaceutically acceptable salts thereof are useful in the treatment of lupus nephritis.

In a further embodiment, the compound of structure (I) and pharmaceutically acceptable salts thereof are useful as antihypertensive agents. For example, in one embodiment, by the administration of a pharmaceutical composition comprising the compound of structure (I) or a pharmaceutically acceptable salt thereof, the blood pressure of a hypertensive mammalian (e.g., human) host is reduced. In one embodiment, they are useful in portal chronic or persistently elevated blood pressure, chronic or persistently elevated blood pressure secondary to treatment with erythropoietin, low renin chronic or persistently elevated blood pressure, and chronic or persistently elevated blood pressure.

In a still further embodiment, the compound of structure (I) and pharmaceutically acceptable salts thereof are useful in the reduction of general morbidity or mortality as a result of the above utilities.

In one embodiment, any of the aforementioned uses or methods of treatment may comprise administering the compound of structure (I), or pharmaceutically acceptable salt thereof, or pharmaceutical composition comprising the same, in combination with one or more other active ingredients, such as other therapeutic or diagnostic agents. For example, in one embodiment, one or more other therapeutic agents may be administered prior to, simultaneously with, or following the administration of the pharmaceutical composition comprising an effective amount of a compound of structure (I), or a pharmaceutically acceptable salt thereof. If formulated as a fixed dose, such combination products may employ the compound of structure (I), or pharmaceutically acceptable salt thereof, within the dosage range described below, and the other active ingredient within its approved dosage range.

In one embodiment, the compound of structure (I), or pharmaceutically acceptable salt thereof, is used in conjunction with hemodialysis.

In a specific embodiment, a method of treating a kidney disease or disorder in a subject in need thereof is provided, the method comprising administering to the subject a pharmaceutical composition comprising a compound having structure (I), or a pharmaceutically acceptable salt thereof, in an amount sufficient to achieve a UP/C ratio of less than or equal to 1.5 g/g. In another embodiment, a method of treating a kidney disease or disorder in a subject in need thereof is provided, the method comprising administering to the subject a pharmaceutical composition comprising a compound having structure (I), or a pharmaceutically acceptable salt thereof, in an amount sufficient to achieve or maintain a UP/C ratio of less than or equal to 1.5 g/g. In another embodiment, a method of treating a kidney disease or disorder in a subject in need thereof is provided, the method comprising administering to the subject a pharmaceutical composition comprising a compound having structure (I), or a pharmaceutically acceptable salt thereof, at a dosing regimen sufficient to achieve or maintain a UP/C ratio of less than or equal to 1.5 g/g. In one embodiment, the dosing regimen comprises administering the compound having structure (I) in an amount of 200 mg/day. In one embodiment, the dosing regimen comprises administering the compound having structure (I) in an amount of 400 mg/day. In one embodiment, the dosing regimen comprises administering the compound having structure (I) in an amount of 800 mg/day. In another embodiment, the dosing regimen comprises administering the compound having structure (I) in an amount of 200 mg/day for 8 weeks, 26 weeks, or 8 months. In another embodiment, the dosing regimen comprises administering the compound having structure (I) in an amount of 400 mg/day for 8 weeks, 26 weeks, or 8 months. In another embodiment, the dosing regimen comprises administering the compound having structure (I) in an amount of 800 mg/day for 8 weeks, 26 weeks, or 8 months.

In another specific embodiment, a method of treating a kidney disease or disorder in a subject in need thereof is provided, the method comprising administering to the subject, over an administration period, a pharmaceutical composition comprising a compound having structure (I), or a pharmaceutically acceptable salt thereof, in an amount sufficient to achieve or maintain a UP/C ratio of less than or equal to 1.5 g/g for at least a portion of the administration period. "Administration period" refers to the time period during which the pharmaceutical composition is administered to the subject. In one embodiment, the administration period is 8 weeks. In one embodiment, the administration period is 26 weeks. In one embodiment, the administration period is 8 months.

In another embodiment, a method of maintaining a UP/C ratio at less than or equal to 1.5 g/g in a subject in need thereof is provided, the method comprising administering to the subject a pharmaceutical composition comprising a compound having structure (I), or a pharmaceutically acceptable salt thereof, in an amount sufficient to maintain a UP/C ratio of less than or equal to 1.5 g/g.

In another embodiment, a method of reducing a UP/C ratio to less than or equal to 1.5 g/g in a subject in need thereof is provided, comprising administering to the subject a pharmaceutical composition comprising a compound having structure (I), or a pharmaceutically acceptable salt thereof, in an amount sufficient to reduce said patient's UP/C ratio to less than or equal to 1.5 g/g. In a further embodiment, the subject has, or has had, a UP/C ratio greater than 1.5 g/g prior to administration of the pharmaceutical composition.

In any of the aforementioned embodiments, the method may achieve a reduction in the subject's UP/C ratio of at least 40% relative to the subject's baseline UP/C ratio.

In any of the aforementioned embodiments, the amount or dosing regimen may be sufficient to achieve a reduction in the subject's UP/C ratio of at least 40% relative to the subject's baseline UP/C ratio.

In any of the aforementioned embodiments, a UP/C ratio of less than or equal to 1.5 g/g may be achieved within 8 weeks of administering the pharmaceutical composition. In any of the aforementioned embodiments, a UP/C ratio of less than or equal to 1.5 g/g may be achieved within 26 weeks of administering the pharmaceutical composition. In any of the aforementioned embodiments, a UP/C ratio of less than or equal to 1.5 g/g may be achieved within 8 months of administering the pharmaceutical composition.

In any of the aforementioned embodiments, the amount of the compound having structure (I), or pharmaceutically acceptable salt thereof, administered to the subject may be from about 50 mg/day to about 1000 mg/day. For example, in one embodiment, the amount of the compound having structure (I), or pharmaceutically acceptable salt thereof, administered to the subject is about 200 mg/day. In another embodiment, the amount of the compound having structure (I), or pharmaceutically acceptable salt thereof, administered to the subject is about 400 mg/day. In another embodiment, the amount of the compound having structure (I), or pharmaceutically acceptable salt thereof, administered to the subject is about 800 mg/day.

In one embodiment, administering comprises (1) an initial administration of the compound having structure (I), or a pharmaceutically acceptable salt thereof, to the subject at an initial dose; and (2) after the initial administration, a subsequent administration of the compound having structure (I), or a pharmaceutically acceptable salt thereof, to the subject at a subsequent dose, wherein the subsequent dose is greater than the initial dose. In a further embodiment, the blood pressure of the subject has been determined to be above 90/60 mmHg before the subsequent administration. In a still further embodiment, the initial dose is 400 mg/day and the subsequent dose is 800 mg/day. In another embodiment, the initial dose is 200 mg/day and the subsequent dose is 400 mg/day. In one embodiment, the initial dose is 200 mg/day and the subsequent dose is 400 mg/day, and the subject is a child weighing less than 50 kg. In one embodiment, the initial dose is 200 mg/day and the subsequent dose is 400 mg/day, and the subject has a blood pressure less than or equal to 90/60 mmHg before the initial administration. In any of the aforementioned embodiments, the initial administration may have a duration of 1-3 weeks. In a specific embodiment, the initial administration has a duration of 2 weeks.

In one embodiment, in the aforementioned methods, said administering comprises (1) an initial administration of the compound having structure (I), or a pharmaceutically acceptable salt thereof, to the subject for 1-3 weeks at 400 mg/day; and (2) after the initial administration, a subsequent administration of the compound having structure (I), or a pharmaceutically acceptable salt thereof, to the subject at 800 mg/day. In a further embodiment, the blood pressure of the subject has been determined to be above 90/60 mmHg before the subsequent administration.

In one embodiment, in the aforementioned methods, said administering comprises (1) an initial administration of the compound having structure (I), or a pharmaceutically acceptable salt thereof, to the subject for 1-3 weeks at 200 mg/day; and (2) after the initial administration, a subsequent administration of the compound having structure (I), or a pharmaceutically acceptable salt thereof, to the subject at 400 mg/day. In a further embodiment, the subject is a child weighing less than 50 kg. In another embodiment, the subject has a blood pressure less than or equal to 90/60 mmHg before the initial administration.

In one embodiment, in the aforementioned methods, said administering comprises (1) an initial administration of the compound having structure (I), or a pharmaceutically acceptable salt thereof, to the subject at an initial dose; and (2) after the initial administration, a subsequent administration of the compound having structure (I), or a pharmaceutically acceptable salt thereof, to the subject at a subsequent dose, wherein the subsequent dose is greater than the initial dose; and the method further comprises measuring the blood pressure of the subject before the subsequent administration. In a further embodiment, the blood pressure of the subject is determined to be above 90/60 mmHg before the subsequent administration. In a further embodiment, the initial dose is 400 mg/day and the subsequent dose is 800 mg/day. In another embodiment, the initial dose is 200 mg/day and the subsequent dose is 400 mg/day. In another embodiment, the initial dose is 200 mg/day and the subsequent dose is 400 mg/day, and the subject is a child weighing less than 50 kg. In another embodiment, the initial dose is 200 mg/day and the subsequent dose is 400 mg/day, and the subject has a blood pressure less than or equal to 90/60 mmHg before the initial administration. In any of the aforementioned embodiments, the initial administration may have a duration of 1-3 weeks. In a specific embodiment, the initial administration has a duration of 2 weeks.

In one embodiment, in the aforementioned methods, said administering comprises (1) an initial administration of the compound having structure (I), or a pharmaceutically acceptable salt thereof, to the subject for 1-3 weeks at 400 mg/day; and (2) after the initial administration, a subsequent administration of the compound having structure (I), or a pharmaceutically acceptable salt thereof, to the subject at 800 mg/day; and the method further comprises measuring the blood pressure of the subject before the subsequent administration. In a further embodiment, the initial administration has a duration of 2 weeks. In a further embodiment, the blood pressure of the subject is determined to be above 90/60 mmHg before the subsequent administration.

In one embodiment, in the aforementioned methods, said administering comprises (1) an initial administration of the compound having structure (I), or a pharmaceutically acceptable salt thereof, to the subject for 1-3 weeks at 200 mg/day; and (2) after the initial administration, a subsequent administration of the compound having structure (I), or a pharmaceutically acceptable salt thereof, to the subject at 400 mg/day; and the method further comprises measuring the blood pressure of the subject before the subsequent administration. In one embodiment, the subject is a child weighing less than 50 kg. In one embodiment, the subject has a blood pressure less than or equal to 90/60 mmHg before the initial administration. In a further embodiment, the initial administration has a duration of 2 weeks.

In any of the aforementioned embodiments, the compound may be a compound having structure (I).

In any of the aforementioned embodiments, the method may further comprise administering to said subject one or more additional therapeutic agents.

In any of the aforementioned embodiments, the subject may have been administered one or more steroids prior to administering the pharmaceutical composition.

In any of the aforementioned embodiments, the subject may have 20% or less interstitial fibrosis.

In any of the aforementioned embodiments, the subject may have 20% or less tubular atrophy.

In any of the aforementioned embodiments, the kidney disease or disorder may be focal segmental glomerulosclerosis (FSGS). In a particular embodiment, the FSGS is primary FSGS. In another embodiment, the FSGS is secondary FSGS. In still another embodiment, the FSGS is genetic FSGS.

In any of the aforementioned embodiments, the kidney disease or disorder may be IgA nephropathy.

In any of the aforementioned embodiments, the kidney disease or disorder may be idiopathic membranous nephropathy (IMN).

In any of the aforementioned embodiments, the kidney disease or disorder may be diabetic nephropathy.

In any of the aforementioned embodiments, the kidney disease or disorder may be Alport syndrome.

In any of the aforementioned embodiments, the kidney disease or disorder may be lupus nephritis.

In any of the aforementioned embodiments, the kidney disease or disorder may be a disorder related to glomerular function.

In some embodiments, the present disclosure provides a pharmaceutical composition comprising a compound having structure (I), or a pharmaceutically acceptable salt thereof, for use in the aforementioned methods.

In some embodiments, the present disclosure provides for the use of a pharmaceutical composition comprising a compound having structure (I), or a pharmaceutically acceptable salt thereof, in the manufacture of a medicament for use in the aforementioned therapeutic methods.

The present disclosure also provides in further embodiments:

1. A method of treating a kidney disease or disorder in a subject in need thereof, the method comprising administering to said subject a pharmaceutical composition comprising a compound having structure (I),

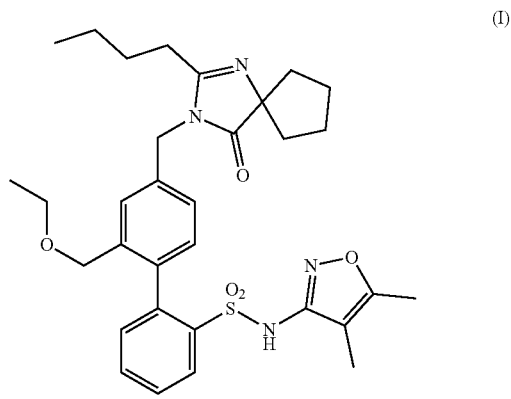 [SMILES: CCCCC1=NC2(CCCC2)C(=O)N1Cc1ccc(-c2ccccc2S(=O)(=O)Nc2noc(C)c2C)c(COCC)c1]

or a pharmaceutically acceptable salt thereof, in an amount sufficient to achieve a urine protein to creatinine ("UP/C") ratio of less than or equal to 1.5 g/g.

2. A method of treating a kidney disease or disorder in a subject in need thereof, the method comprising administering to said subject a pharmaceutical composition comprising a compound having structure (I),

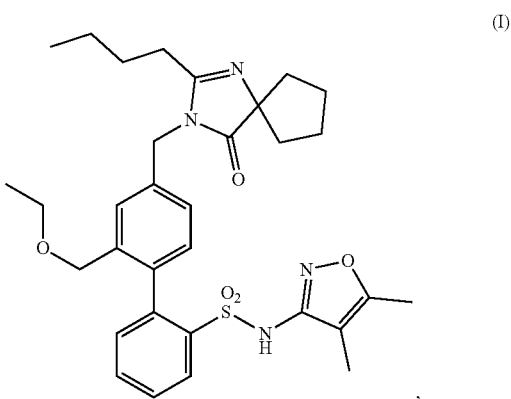 [SMILES: CCCCC1=NC2(CCCC2)C(=O)N1Cc1ccc(-c2ccccc2S(=O)(=O)Nc2noc(C)c2C)c(COCC)c1]

or a pharmaceutically acceptable salt thereof, in an amount sufficient to achieve or maintain a UP/C ratio of less than or equal to 1.5 g/g.

3. A method of treating a kidney disease or disorder in a subject in need thereof, the method comprising administering to said subject a pharmaceutical composition comprising a compound having structure (I),

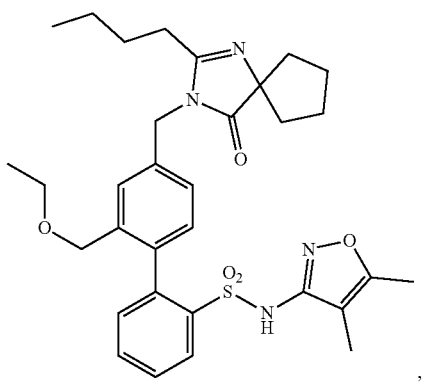

or a pharmaceutically acceptable salt thereof, at a dosing regimen sufficient to achieve or maintain a UP/C ratio of less than or equal to 1.5 g/g.

4. A method of treating a kidney disease or disorder in a subject in need thereof, the method comprising administering to said subject, over an administration period, a pharmaceutical composition comprising a compound having structure (I),

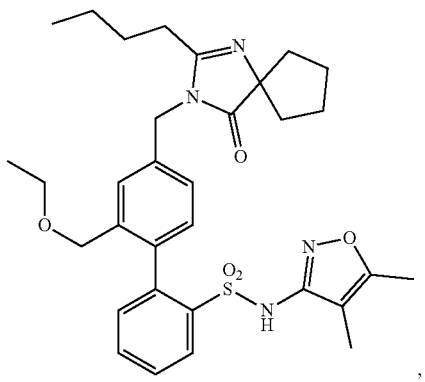

or a pharmaceutically acceptable salt thereof, in an amount sufficient to achieve or maintain a UP/C ratio of less than or equal to 1.5 g/g for at least a portion of said administration period.

5. A method of maintaining a UP/C ratio at less than or equal to 1.5 g/g in a subject in need thereof, the method comprising administering to said subject a pharmaceutical composition comprising a compound having structure (I),

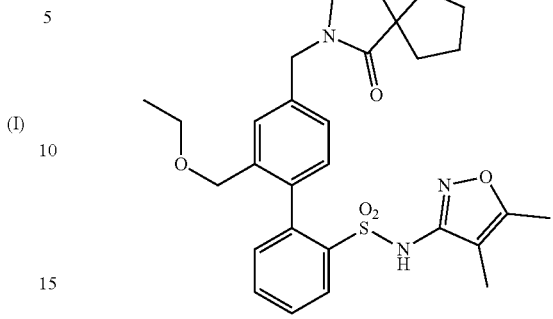

or a pharmaceutically acceptable salt thereof, in an amount sufficient to maintain a UP/C ratio of less than or equal to 1.5 g/g.

6. A method of reducing a UP/C ratio to less than or equal to 1.5 g/g in a subject in need thereof, comprising administering to said subject a pharmaceutical composition comprising a compound having structure (I),

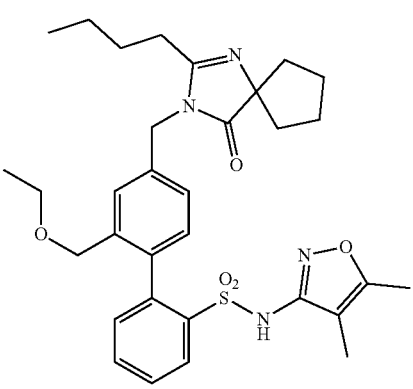

or a pharmaceutically acceptable salt thereof, in an amount sufficient to reduce said patient's UP/C ratio to less than or equal to 1.5 g/g.

7. The method according to any preceding embodiment, wherein said subject has, or has had, a UP/C ratio greater than 1.5 g/g prior to administration of said pharmaceutical composition.

8. The method according to any preceding embodiment, wherein the method achieves a reduction in said subject's UP/C ratio of at least 40% relative to said subject's baseline UP/C ratio.

9. The method according to any preceding embodiment, wherein a UP/C ratio of less than or equal to 1.5 g/g is achieved within 8 weeks of administering said pharmaceutical composition.

10. The method according to any preceding embodiment, wherein a UP/C ratio of less than or equal to 1.5 g/g is achieved within 26 weeks of administering said pharmaceutical composition.

11. The method according to any preceding embodiment, wherein a UP/C ratio of less than or equal to 1.5 g/g is achieved within 8 months of administering said pharmaceutical composition.

12. The method according to embodiment 4, wherein said administration period is 8 weeks.

13. The method according to embodiment 4, wherein said administration period is 26 weeks.

14. The method according to embodiment 4, wherein said administration period is 8 months.

15. The method according to any preceding embodiment, wherein the amount of said compound having structure (I), or pharmaceutically acceptable salt thereof, administered to said subject is from about 50 mg/day to about 1000 mg/day.

16. The method according to embodiment 15, wherein the amount of the compound having structure (I), or pharmaceutically acceptable salt thereof, administered to said subject is from about 200 mg/day to about 800 mg/day.

17. The method according to embodiment 15, wherein the amount of said compound having structure (I), or pharmaceutically acceptable salt thereof, administered to said subject is about 200 mg/day.

18. The method according to embodiment 15, wherein the amount of said compound having structure (I), or pharmaceutically acceptable salt thereof, administered to said subject is about 400 mg/day.

19. The method according to embodiment 15, wherein the amount of said compound having structure (I), or pharmaceutically acceptable salt thereof, administered to said subject is about 800 mg/day.

20. The method according to any one of embodiment 1-14, wherein said administering comprises (1) an initial administration of said compound having structure (I), or a pharmaceutically acceptable salt thereof, to said subject at an initial dose; and (2) after said initial administration, a subsequent administration of said compound having structure (I), or a pharmaceutically acceptable salt thereof, to said subject at a subsequent dose, wherein said subsequent dose is greater than said initial dose.

21. The method according to embodiment 20, wherein said initial dose is 400 mg/day and said subsequent dose is 800 mg/day.

22. The method according to embodiment 20, wherein said initial dose is 200 mg/day and said subsequent dose is 400 mg/day.

23. The method according to embodiment 22, wherein said subject is a child weighing less than 50 kg.

24. The method according to any one of embodiments 20-23, wherein said initial administration has a duration of 2 weeks.

25. The method according to any one of embodiments 1-14, wherein said administering comprises (1) an initial administration of said compound having structure (I), or a pharmaceutically acceptable salt thereof, to said subject for 1-3 weeks at 400 mg/day; and (2) after said initial administration, a subsequent administration of said compound having structure (I), or a pharmaceutically acceptable salt thereof, to said subject at 800 mg/day.

26. The method according to any one of embodiments 1-14, wherein said administering comprises (1) an initial administration of said compound having structure (I), or a pharmaceutically acceptable salt thereof, to said subject for 1-3 weeks at 200 mg/day; and (2) after said initial administration, a subsequent administration of said compound having structure (I), or a pharmaceutically acceptable salt thereof, to said subject at 400 mg/day.

27. The method according to embodiment 26, wherein said subject is a child weighing less than 50 kg.

28. The method according to any one of embodiments 1-14:

wherein said administering comprises (1) an initial administration of said compound having structure (I), or a pharmaceutically acceptable salt thereof, to said subject at an initial dose; and (2) after said initial administration, a subsequent administration of said compound having structure (I), or a pharmaceutically acceptable salt thereof, to said subject at a subsequent dose, wherein said subsequent dose is greater than said initial dose; and the method further comprises measuring the blood pressure of said subject before the subsequent administration.

29. The method according to embodiment 28, wherein said initial dose is 400 mg/day and said subsequent dose is 800 mg/day.

30. The method according to embodiment 28, wherein said initial dose is 200 mg/day and said subsequent dose is 400 mg/day.

31. The method according to embodiment 30, wherein said subject is a child weighing less than 50 kg.

32. The method according to any one of embodiments 28-31, wherein said initial administration has a duration of 1-3 weeks.

33. The method according to any one of embodiments 1-14:

wherein said administering comprises (1) an initial administration of said compound having structure (I), or a pharmaceutically acceptable salt thereof, to said subject for 1-3 weeks at 400 mg/day; and (2) after said initial administration, a subsequent administration of said compound having structure (I), or a pharmaceutically acceptable salt thereof, to said subject at 800 mg/day; and the method further comprises measuring the blood pressure of said subject before said subsequent administration.

34. The method according to any one of embodiments 1-14:

wherein said administering comprises (1) an initial administration of said compound having structure (I), or a pharmaceutically acceptable salt thereof, to said subject for 1-3 weeks at 200 mg/day; and (2) after said initial administration, a subsequent administration of said compound having structure (I), or a pharmaceutically acceptable salt thereof, to said subject at 400 mg/day; and the method further comprises measuring the blood pressure of said subject before said subsequent administration.

35. The method according to embodiment 34, wherein said subject is a child weighing less than 50 kg.

36. The method according to any preceding embodiment, wherein said compound has structure (I).

37. The method according to any preceding embodiment, further comprising administering to said subject one or more additional therapeutic agents.

38. The method according to any preceding embodiment, wherein said kidney disease or disorder is focal segmental glomerulosclerosis (FSGS).

39. The method according to embodiment 38, wherein said FSGS is primary FSGS.

40. The method according to embodiment 38, wherein said FSGS is secondary FSGS.

41. The method according to embodiment 38, wherein said FSGS is genetic FSGS.

42. The method according to any one of embodiments 1-37, wherein said kidney disease or disorder is IgA nephropathy.

43. The method according to any one of embodiments 1-37, wherein said kidney disease or disorder is idiopathic membranous nephropathy (IMN).

44. The method according to any one of embodiments 1-37, wherein said kidney disease or disorder is diabetic nephropathy.

45. A pharmaceutical composition comprising a compound having structure (I),

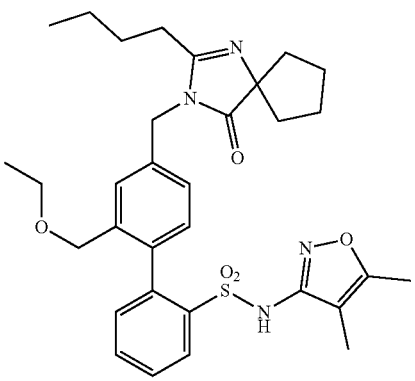

(I)

or a pharmaceutically acceptable salt thereof, for use in a method of treating a kidney disease or disorder in a subject in need thereof, the method comprising administering to said subject said pharmaceutical composition (i) in an amount sufficient to achieve a urine protein to creatinine ("UP/C") ratio of less than or equal to 1.5 g/g;

(ii) in an amount sufficient to achieve or maintain a UP/C ratio of less than or equal to 1.5 g/g; or (iii) at a dosing regimen sufficient to achieve or maintain a UP/C ratio of less than or equal to 1.5 g/g.

46. The pharmaceutical composition for use according to embodiment 45, wherein the pharmaceutical composition is administered to said subject over an administration period in an amount sufficient to achieve or maintain a UP/C ratio of less than or equal to 1.5 g/g for at least a portion of said administration period.

47. A pharmaceutical composition comprising a compound having structure (I),

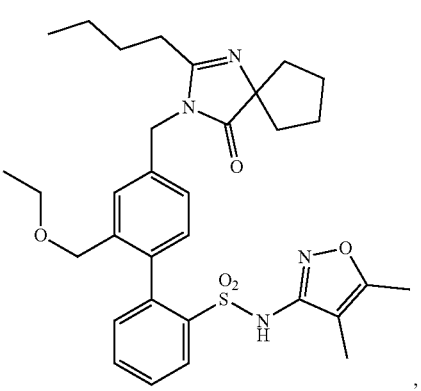

(I)

or a pharmaceutically acceptable salt thereof, for use in a therapeutic method of (i) maintaining a UP/C ratio at less than or equal to 1.5 g/g in a subject in need thereof, the method comprising administering to said subject said pharmaceutical composition in an amount sufficient to maintain a UP/C ratio of less than or equal to 1.5 g/g; or (ii) reducing a UP/C ratio to less than or equal to 1.5 g/g in a subject in need thereof, the method comprising administering to said subject said pharmaceutical composition in an amount sufficient to reduce said patient's UP/C ratio to less than or equal to 1.5 g/g.

48. The pharmaceutical composition for use according to any one of embodiments 45-47, wherein said subject has, or has had, a UP/C ratio greater than 1.5 g/g prior to administration of said pharmaceutical composition.

49. The pharmaceutical composition for use according to any one of embodiments 45-48, wherein the method achieves a reduction in said subject's UP/C ratio of at least 40% relative to said subject's baseline UP/C ratio.

50. The pharmaceutical composition for use according to any one of embodiments 45-49, wherein a UP/C ratio of less than or equal to 1.5 g/g is achieved within 8 weeks of administering said pharmaceutical composition.

51. The pharmaceutical composition for use according to any one of embodiments 45-50, wherein a UP/C ratio of less than or equal to 1.5 g/g is achieved within 26 weeks of administering said pharmaceutical composition.

52. The pharmaceutical composition for use according to any one of embodiments 45-51, wherein a UP/C ratio of less than or equal to 1.5 g/g is achieved within 8 months of administering said pharmaceutical composition.

53. The pharmaceutical composition for use according to embodiment 46, wherein said administration period is 8 weeks.

54. The pharmaceutical composition for use according to embodiment 46, wherein said administration period is 26 weeks.

55. The pharmaceutical composition for use according to embodiment 46, wherein said administration period is 8 months.

56. The pharmaceutical composition for use according to any one of embodiments 45-55, wherein the amount of said compound having structure (I), or pharmaceutically acceptable salt thereof, administered to said subject is from about 50 mg/day to about 1000 mg/day.

57. The pharmaceutical composition for use according to embodiment 56, wherein the amount of the compound having structure (I), or pharmaceutically acceptable salt thereof, administered to said subject is from about 200 mg/day to about 800 mg/day.

58. The pharmaceutical composition for use according to embodiment 56, wherein the amount of said compound having structure (I), or pharmaceutically acceptable salt thereof, administered to said subject is about 200 mg/day.

59. The pharmaceutical composition for use according to embodiment 56, wherein the amount of said compound having structure (I), or pharmaceutically acceptable salt thereof, administered to said subject is about 400 mg/day.

60. The pharmaceutical composition for use according to embodiment 56, wherein the amount of said compound having structure (I), or pharmaceutically acceptable salt thereof, administered to said subject is about 800 mg/day.

61. The pharmaceutical composition for use according to any one of embodiments 45-55, wherein said administering comprises (1) an initial administration of said compound having structure (I), or a pharmaceutically acceptable salt thereof, to said subject at an initial dose; and (2) after said initial administration, a subsequent administration of said compound having structure (I), or a pharmaceutically acceptable salt thereof, to said subject at a subsequent dose, wherein said subsequent dose is greater than said initial dose.

62. The pharmaceutical composition for use according to embodiment 61, wherein said initial dose is 400 mg/day and said subsequent dose is 800 mg/day.

63. The pharmaceutical composition for use according to embodiment 61, wherein said initial dose is 200 mg/day and said subsequent dose is 400 mg/day.

64. The pharmaceutical composition for use according to embodiment 63, wherein said subject is a child weighing less than 50 kg.

65. The pharmaceutical composition for use according to any one of embodiments 61-64, wherein said initial administration has a duration of 2 weeks.

66. The pharmaceutical composition for use according to any one of embodiments 45-55, wherein said administering comprises (1) an initial administration of said compound having structure (I), or a pharmaceutically acceptable salt thereof, to said subject for 1-3 weeks at 400 mg/day; and (2) after said initial administration, a subsequent administration of said compound having structure (I), or a pharmaceutically acceptable salt thereof, to said subject at 800 mg/day.

67. The pharmaceutical composition for use according to any one of embodiments 45-55, wherein said administering comprises (1) an initial administration of said compound having structure (I), or a pharmaceutically acceptable salt thereof, to said subject for 1-3 weeks at 200 mg/day; and (2) after said initial administration, a subsequent administration of said compound having structure (I), or a pharmaceutically acceptable salt thereof, to said subject at 400 mg/day.

68. The pharmaceutical composition for use according to embodiment 67, wherein said subject is a child weighing less than 50 kg.

69. The pharmaceutical composition for use according to any one of embodiments 45-55:
wherein said administering comprises (1) an initial administration of said compound having structure (I), or a pharmaceutically acceptable salt thereof, to said subject at an initial dose; and (2) after said initial administration, a subsequent administration of said compound having structure (I), or a pharmaceutically acceptable salt thereof, to said subject at a subsequent dose, wherein said subsequent dose is greater than said initial dose; and the method further comprises measuring the blood pressure of said subject before the subsequent administration.

70. The pharmaceutical composition for use according to embodiment 69, wherein said initial dose is 400 mg/day and said subsequent dose is 800 mg/day.

71. The pharmaceutical composition for use according to embodiment 69, wherein said initial dose is 200 mg/day and said subsequent dose is 400 mg/day.

72. The pharmaceutical composition for use according to embodiment 71, wherein said subject is a child weighing less than 50 kg.

73. The pharmaceutical composition for use according to any one of embodiments 69-72, wherein said initial administration has a duration of 1-3 weeks.

74. The pharmaceutical composition for use according to any one of embodiments 45-55:
wherein said administering comprises (1) an initial administration of said compound having structure (I), or a pharmaceutically acceptable salt thereof, to said subject for 1-3 weeks at 400 mg/day; and (2) after said initial administration, a subsequent administration of said compound having structure (I), or a pharmaceutically acceptable salt thereof, to said subject at 800 mg/day; and
the method further comprises measuring the blood pressure of said subject before said subsequent administration.

75. The pharmaceutical composition for use according to any one of embodiments 45-55:
wherein said administering comprises (1) an initial administration of said compound having structure (I), or a pharmaceutically acceptable salt thereof, to said subject for 1-3 weeks at 200 mg/day; and (2) after said initial administration, a subsequent administration of said compound having structure (I), or a pharmaceutically acceptable salt thereof, to said subject at 400 mg/day; and
the method further comprises measuring the blood pressure of said subject before said subsequent administration.

76. The pharmaceutical composition for use according to embodiment 75, wherein said subject is a child weighing less than 50 kg.

77. The pharmaceutical composition for use according to any one of embodiments 45-76, wherein said compound has structure (I).

78. The pharmaceutical composition for use according to any one of embodiments 45-77, further comprising administering to said subject one or more additional therapeutic agents.

79. The pharmaceutical composition for use according to any one of embodiments 45-78, wherein said kidney disease or disorder is focal segmental glomerulosclerosis (FSGS).

80. The pharmaceutical composition for use according to embodiment 79, wherein said FSGS is primary FSGS.

81. The pharmaceutical composition for use according to embodiment 79, wherein said FSGS is secondary FSGS.

82. The pharmaceutical composition for use according to embodiment 79, wherein said FSGS is genetic FSGS.

83. The pharmaceutical composition for use according to any one of embodiments 45-78, wherein said kidney disease or disorder is IgA nephropathy.

84. The pharmaceutical composition for use according to any one of embodiments 45-78, wherein said kidney disease or disorder is idiopathic membranous nephropathy (IMN).

85. The pharmaceutical composition for use according to any one of embodiments 45-78, wherein said kidney disease or disorder is diabetic nephropathy.

86. Use of a pharmaceutical composition comprising a compound having structure (I),

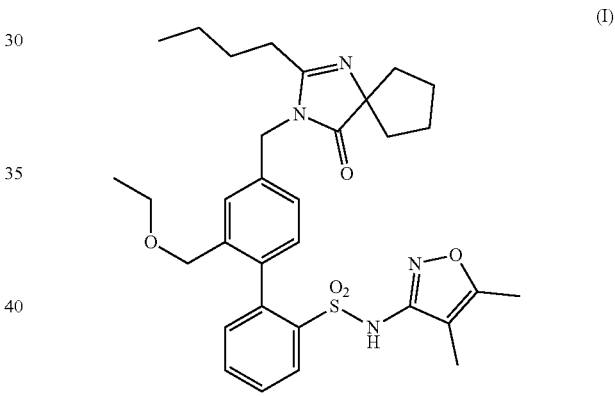

or a pharmaceutically acceptable salt thereof, in the manufacture of a medicament for use in a method of treating a kidney disease or disorder in a subject in need thereof, the method comprising administering to said subject said pharmaceutical composition (i) in an amount sufficient to achieve a urine protein to creatinine ("UP/C") ratio of less than or equal to 1.5 g/g;

(ii) in an amount sufficient to achieve or maintain a UP/C ratio of less than or equal to 1.5 g/g; or (iii) at a dosing regimen sufficient to achieve or maintain a UP/C ratio of less than or equal to 1.5 g/g.

87. The use in the manufacture of a medicament according to embodiment 86, wherein the pharmaceutical composition is administered to said subject over an administration period in an amount sufficient to achieve or maintain a UP/C ratio of less than or equal to 1.5 g/g for at least a portion of said administration period.

88. Use of a pharmaceutical composition comprising a compound having structure (I),

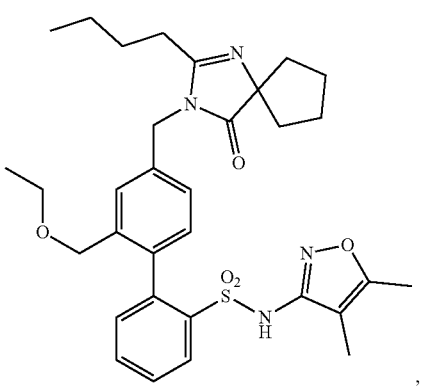
(I)

or a pharmaceutically acceptable salt thereof, in the manufacture of a medicament for for use in a therapeutic method of
(i) maintaining a UP/C ratio at less than or equal to 1.5 g/g in a subject in need thereof, the method comprising administering to said subject said pharmaceutical composition in an amount sufficient to maintain a UP/C ratio of less than or equal to 1.5 g/g; or
(ii) reducing a UP/C ratio to less than or equal to 1.5 g/g in a subject in need thereof, the method comprising administering to said subject said pharmaceutical composition in an amount sufficient to reduce said patient's UP/C ratio to less than or equal to 1.5 g/g.

89. The use in the manufacture of a medicament according to any one of embodiments 86-88, wherein said subject has, or has had, a UP/C ratio greater than 1.5 g/g prior to administration of said pharmaceutical composition.

90. The use in the manufacture of a medicament according to any one of embodiments 86-89, wherein the method achieves a reduction in said subject's UP/C ratio of at least 40% relative to said subject's baseline UP/C ratio.

91. The use in the manufacture of a medicament according to any one of embodiments 86-90, wherein a UP/C ratio of less than or equal to 1.5 g/g is achieved within 8 weeks of administering said pharmaceutical composition.

92. The use in the manufacture of a medicament according to any one of embodiments 86-91, wherein a UP/C ratio of less than or equal to 1.5 g/g is achieved within 26 weeks of administering said pharmaceutical composition.

93. The use in the manufacture of a medicament according to any one of embodiments 86-92, wherein a UP/C ratio of less than or equal to 1.5 g/g is achieved within 8 months of administering said pharmaceutical composition.

94. The use in the manufacture of a medicament according to embodiment 87, wherein said administration period is 8 weeks.

95. The use in the manufacture of a medicament according to embodiment 87, wherein said administration period is 26 weeks.

96. The use in the manufacture of a medicament according to embodiment 87, wherein said administration period is 8 months.

97. The use in the manufacture of a medicament according to any one of embodiments 86-96, wherein the amount of said compound having structure (I), or pharmaceutically acceptable salt thereof, administered to said subject is from about 50 mg/day to about 1000 mg/day.

98. The use in the manufacture of a medicament according to embodiment 97, wherein the amount of the compound having structure (I), or pharmaceutically acceptable salt thereof, administered to said subject is from about 200 mg/day to about 800 mg/day.

99. The use in the manufacture of a medicament according to embodiment 97, wherein the amount of said compound having structure (I), or pharmaceutically acceptable salt thereof, administered to said subject is about 200 mg/day.

100. The use in the manufacture of a medicament according to embodiment 97, wherein the amount of said compound having structure (I), or pharmaceutically acceptable salt thereof, administered to said subject is about 400 mg/day.

101. The use in the manufacture of a medicament according to embodiment 97, wherein the amount of said compound having structure (I), or pharmaceutically acceptable salt thereof, administered to said subject is about 800 mg/day.

102. The use in the manufacture of a medicament according to any one of embodiments 86-96, wherein said administering comprises (1) an initial administration of said compound having structure (I), or a pharmaceutically acceptable salt thereof, to said subject at an initial dose; and (2) after said initial administration, a subsequent administration of said compound having structure (I), or a pharmaceutically acceptable salt thereof, to said subject at a subsequent dose, wherein said subsequent dose is greater than said initial dose.

103. The use in the manufacture of a medicament according to embodiment 102, wherein said initial dose is 400 mg/day and said subsequent dose is 800 mg/day.

104. The use in the manufacture of a medicament use according to embodiment 102, wherein said initial dose is 200 mg/day and said subsequent dose is 400 mg/day.

105. The use in the manufacture of a medicament according to embodiment 104, wherein said subject is a child weighing less than 50 kg.

106. The use in the manufacture of a medicament according to any one of embodiments 102-105, wherein said initial administration has a duration of 2 weeks.

107. The use in the manufacture of a medicament according to any one of embodiments 86-96, wherein said administering comprises (1) an initial administration of said compound having structure (I), or a pharmaceutically acceptable salt thereof, to said subject for 1-3 weeks at 400 mg/day; and (2) after said initial administration, a subsequent administration of said compound having structure (I), or a pharmaceutically acceptable salt thereof, to said subject at 800 mg/day.

108. The use in the manufacture of a medicament according to any one of embodiments 86-96, wherein said administering comprises (1) an initial administration of said compound having structure (I), or a pharmaceutically acceptable salt thereof, to said subject for 1-3 weeks at 200 mg/day; and (2) after said initial administration, a subsequent administration of said compound having structure (I), or a pharmaceutically acceptable salt thereof, to said subject at 400 mg/day.

109. The use in the manufacture of a medicament according to embodiment 108, wherein said subject is a child weighing less than 50 kg.

110. The use in the manufacture of a medicament according to any one of embodiments 86-96:
wherein said administering comprises (1) an initial administration of said compound having structure (I), or a pharmaceutically acceptable salt thereof, to said subject at an initial dose; and (2) after said initial administration, a subsequent administration of said compound having structure (I), or a pharmaceutically acceptable salt thereof, to said subject at a subsequent dose, wherein said subsequent dose is greater than said initial dose; and the method further comprises measuring the blood pressure of said subject before the subsequent administration.

111. The use in the manufacture of a medicament according to embodiment 110, wherein said initial dose is 400 mg/day and said subsequent dose is 800 mg/day.

112. The use in the manufacture of a medicament according to embodiment 110, wherein said initial dose is 200 mg/day and said subsequent dose is 400 mg/day.

113. The use in the manufacture of a medicament according to embodiment 112, wherein said subject is a child weighing less than 50 kg.

114. The use in the manufacture of a medicament according to any one of embodiments 110-113, wherein said initial administration has a duration of 1-3 weeks.

115. The use in the manufacture of a medicament according to any one of embodiments 86-96:
wherein said administering comprises (1) an initial administration of said compound having structure (I), or a pharmaceutically acceptable salt thereof, to said subject for 1-3 weeks at 400 mg/day; and (2) after said initial administration, a subsequent administration of said compound having structure (I), or a pharmaceutically acceptable salt thereof, to said subject at 800 mg/day; and
the method further comprises measuring the blood pressure of said subject before said subsequent administration.

116. The use in the manufacture of a medicament according to any one of embodiments 86-96:
wherein said administering comprises (1) an initial administration of said compound having structure (I), or a pharmaceutically acceptable salt thereof, to said subject for 1-3 weeks at 200 mg/day; and (2) after said initial administration, a subsequent administration of said compound having structure (I), or a pharmaceutically acceptable salt thereof, to said subject at 400 mg/day; and
the method further comprises measuring the blood pressure of said subject before said subsequent administration.

117. The use in the manufacture of a medicament according to embodiment 116, wherein said subject is a child weighing less than 50 kg.

118. The use in the manufacture of a medicament according to any one of embodiments 86-117, wherein said compound has structure (I).

119. The use in the manufacture of a medicament according to any one of embodiments 86-118, further comprising administering to said subject one or more additional therapeutic agents.

120. The use in the manufacture of a medicament according to any one of embodiments 86-119, wherein said kidney disease or disorder is focal segmental glomerulosclerosis (FSGS).

121. The use in the manufacture of a medicament according to embodiment 120, wherein said FSGS is primary FSGS.

122. The use in the manufacture of a medicament according to embodiment 120, wherein said FSGS is secondary FSGS.

123. The use in the manufacture of a medicament according to embodiment 120, wherein said FSGS is genetic FSGS.

124. The use in the manufacture of a medicament according to any one of embodiments 86-119, wherein said kidney disease or disorder is IgA nephropathy.

125. The use in the manufacture of a medicament according to any one of embodiments 86-119, wherein said kidney disease or disorder is idiopathic membranous nephropathy (IMN).

126. The use in the manufacture of a medicament according to any one of embodiments 86-119, wherein said kidney disease or disorder is diabetic nephropathy.

127. The method, pharmaceutical composition for use, or use in the manufacture of a medicament according to any one of embodiments 1-37, 45-78, and 86-119, wherein said kidney disease or disorder is a disorder related to glomerular function.

128. The method, pharmaceutical composition for use, or use in the manufacture of a medicament according to any one of embodiments 1-37, 45-78, and 86-119, wherein said kidney disease or disorder is Alport syndrome.

129. The method, pharmaceutical composition for use, or use in the manufacture of a medicament according to any one of embodiments 1-37, 45-78, and 86-119, wherein said kidney disease or disorder is lupus nephritis.

Pharmaceutical Formulations

In one aspect, the present disclosure relates to the administration of a pharmaceutical composition comprising the compound of structure (I), or a pharmaceutically acceptable salt thereof, and pharmaceutically acceptable excipient. Techniques for formulation and administration of the compound of structure (I), or pharmaceutically acceptable salt thereof, may be found, for example, in "Remington's Pharmaceutical Sciences," Mack Publishing Co., Easton, Pa., 18th edition, 1990. In some embodiments, the pharmaceutical composition is formulated as described below.

In some embodiments, an excipient includes any substance, not itself a therapeutic agent, used as a carrier, diluent, adjuvant, or vehicle for delivery of a therapeutic agent to a subject or added to a pharmaceutical composition to improve its handling or storage properties or to permit or facilitate formation of a dose unit of the composition into a discrete article such as a capsule, tablet, film coated tablet, caplet, gel cap, pill, pellet, bead, and the like suitable for oral administration. For example, an excipient may be a surface active agent (or "surfactant"), carrier, diluent, disintegrant, binding agent, wetting agent, polymer, lubricant, glidant, coating or coating assistant, film forming substance, sweetener, solubilizing agent, smoothing agent, suspension agent, substance added to mask or counteract a disagreeable taste or odor, flavor, colorant, fragrance, or substance added to improve appearance of the composition, or a combination thereof.

Acceptable excipients include, for example, microcrystalline cellulose, lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, polyvinyl alcohol, saline, dextrose, mannitol, lactose monohydrate, lecithin, albumin, sodium glutamate, cysteine hydrochloride, croscarmellose sodium, sodium starch glycolate, hydroxypropyl cellulose, poloxamer (e.g., poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, and poloxamer 105 benzoate, poloxamer 182 dibenzoate 407, and the like), sodium lauryl sulfate, colloidal silicon dioxide, and the like. Examples of suitable excipients for tablets and capsules include microcrystalline cellulose, silicified microcrystalline cellulose, lactose monohydrate, croscarmellose sodium, sodium starch, hydroxypropyl cellulose, poloxamer 188, sodium lauryl sulfate, colloidal silicon dioxide, and magnesium stearate. Examples of suitable excipients for soft gelatin capsules include vegetable oils, waxes, fats, and semisolid and liquid polyols. Suitable excipients for the preparation of solutions and syrups include, for example, water, polyols, sucrose, invert sugar, and glucose. The compound can also be made in microencapsulated form. If desired, absorption enhancing preparations (for example, liposomes), can be utilized. Acceptable excipients for therapeutic use are well known in the pharmaceutical art, and are described, for example, in "Handbook of Pharmaceutical Excipients," 5th edition (Raymond C Rowe, Paul J Sheskey and Sian C Owen, eds.

2005), and "Remington: The Science and Practice of Pharmacy," 21st edition (Lippincott Williams & Wilkins, 2005).

In some embodiments, surfactants are used. The use of surfactants as wetting agents in oral drug forms is described in the literature, for example in H. Sucker, P. Fuchs, P. Speiser, *Pharmazeutische Technologie,* 2nd edition, Thieme 1989, page 260. It is known from other papers, such as published in *Advanced Drug Delivery Reviews* (1997), 23, pages 163-183, that it is also possible to use surfactants, inter alia, to improve the permeation and bioavailability of pharmaceutical active compounds. Examples of surfactants include anionic surfactants, non-ionic surfactants, zwitterionic surfactants, and a mixture thereof. In some embodiments, the surfactant is selected from the group consisting of poly(oxyethylene) sorbitan fatty acid ester, poly(oxyethylene) stearate, poly(oxyethylene) alkyl ether, polyglycolated glyceride, poly(oxyethylene) castor oil, sorbitan fatty acid ester, poloxamer, fatty acid salt, bile salt, alkyl sulfate, lecithin, mixed micelle of bile salt and lecithin, glucose ester vitamin E TPGS (D-α-tocopheryl polyethylene glycol 1000 succinate), sodium lauryl sulfate, and the like, and a mixture thereof.

As used herein, the term "carrier" defines a chemical compound that facilitates the incorporation of a compound into cells or tissues. For example, dimethyl sulfoxide (DMSO) is a commonly utilized carrier, as it facilitates the uptake of many organic compounds into the cells or tissues of an organism. As used herein, the term "diluent" defines chemical compounds diluted in water that will dissolve the compound of interest as well as stabilize the biologically active form of the compound. Salts dissolved in buffered solutions are commonly utilized as diluents in the art. One commonly used buffered solution is phosphate buffered saline because it mimics the salt conditions of human blood. Because buffer salts can control the pH of a solution at low concentrations, a buffered diluent rarely modifies the biological activity of a compound. In some embodiments, a diluent selected from one or more of the compounds sucrose, fructose, glucose, galactose, lactose, maltose, invert sugar, calcium carbonate, lactose, starch, microcrystalline cellulose, lactose monohydrate, calcium hydrogen phosphate, anhydrous calcium hydrogen phosphate, a pharmaceutically acceptable polyol such as xylitol, sorbitol, maltitol, mannitol, isomalt, and glycerol, polydextrose, starch, and the like, or any mixture thereof, is used. Acceptable carriers or diluents for therapeutic use are well known in the pharmaceutical art, and are described, for example, in "Remington's Pharmaceutical Sciences," 18th Ed., Mack Publishing Co., Easton, Pa. (1990).

In some embodiments, disintegrants such as starches, clays, celluloses, algins, gums, or crosslinked polymers are used, for example, to facilitate tablet disintegration after administration. Suitable disintegrants include, for example, crosslinked polyvinylpyrrolidone (PVP-XL), sodium starch glycolate, alginic acid, methacrylic acid DYB, microcrystalline cellulose, crospovidone, polacriline potassium, sodium starch glycolate, starch, pregelatinized starch, croscarmellose sodium, and the like. In some embodiments, the formulation can also contain minor amounts of nontoxic auxiliary substances such as wetting or emulsifying agents, pH buffering agents, and the like; for example, sodium acetate, sorbitan monolaurate, triethanolamine sodium acetate, triethanolamine oleate, sodium lauryl sulfate, dioctyl sodium sulfosuccinate, polyoxyethylene sorbitan fatty acid esters, and the like.

In some embodiments, binders are used, for example, to impart cohesive qualities to a formulation, and thus ensure that the resulting dosage form remains intact after compaction. Suitable binder materials include, but are not limited to, microcrystalline cellulose, gelatin, sugars (including, for example, sucrose, glucose, dextrose and maltodextrin), polyethylene glycol, waxes, natural and synthetic gums, polyvinylpyrrolidone, pregelatinized starch, povidone, cellulosic polymers (including, for example, hydroxypropyl cellulose (HPC), hydroxypropyl methylcellulose (HPMC), methyl cellulose, hydroxyethyl cellulose, and the like), and the like. Accordingly, in some embodiments, a formulations disclosed herein includes at least one binder to enhance the compressibility of the major excipient(s). For example, the formulation can include at least one of the following binders in the following ranges: from about 2% to about 6% w/w hydroxypropyl cellulose (Klucel); from about 2% to about 5% w/w polyvinylpyrrolidone (PVP); from about 1% to about 5% w/w methylcellulose; from about 2% to about 5% hydroxypropyl methylcellulose; from about 1% to about 5% w/w ethylcellulose; from about 1% to about 5% w/w sodium carboxy methylcellulose; and the like. One of ordinary skill in the art would recognize additional binders and/or amounts that can be used in the formulations described herein. As would be recognized by one of ordinary skill in the art, when incorporated into the formulations disclosed herein, the amounts of the major filler(s) and/or other excipients can be reduced accordingly to accommodate the amount of binder added in order to keep the overall unit weight of the dosage form unchanged. In one embodiment, a binder is sprayed on from solution, e.g., wet granulation, to increase binding activity.

In one embodiment, a lubricant is employed in the manufacture of certain dosage forms. For example, a lubricant may be employed when producing tablets. In one embodiment, a lubricant can be added just before the tableting step, and can be mixed with the other ingredients for a minimum period of time to obtain good dispersal. In some embodiments, one or more lubricants may be used. Examples of suitable lubricants include magnesium stearate, calcium stearate, zinc stearate, stearic acid, talc, glyceryl behenate, polyethylene glycol, polyethylene oxide polymers (for example, available under the registered trademarks of Carbowax® for polyethylene glycol and Polyox® for polyethylene oxide from Dow Chemical Company, Midland, Mich.), sodium lauryl sulfate, magnesium lauryl sulfate, sodium oleate, sodium stearyl fumarate, DL-leucine, colloidal silica, and others as known in the art. Typical lubricants are magnesium stearate, calcium stearate, zinc stearate, and mixtures of magnesium stearate with sodium lauryl sulfate. Lubricants may comprise from about 0.25% to about 50% of the tablet weight, typically from about 1% to about 40%, more typically from about 5% to about 30%, and most typically from 20% to 30%. In some embodiments, magnesium stearate can be added as a lubricant, for example, to improve powder flow, prevent the blend from adhering to tableting equipment and punch surfaces, and provide lubrication to allow tablets to be cleanly ejected from tablet dies. In some embodiments, magnesium stearate may be added to pharmaceutical formulations at concentrations ranging from about 0.1% to about 5.0% w/w, or from about 0.25% to about 4% w/w, or from about 0.5% w/w to about 3% w/w, or from about 0.75% to about 2% w/w, or from about 0.8% to about 1.5% w/w, or from about 0.85% to about 1.25% w/w, or from about 0.9% to about 1.20% w/w, or from about 0.85% to about 1.15% w/w, or from about 0.90% to about 1.1.% w/w, or from about 0.95% to about 1.05% w/w, or from about 0.95% to about 1% w/w. The above ranges are examples of typical ranges. One of ordinary skill in the art would recognize additional lubricants and/or amounts that can be used in the formulations described herein. As would be recognized by one of ordinary skill in the art, when incorporated into the pharmaceutical compositions disclosed herein, the amounts of the major filler(s) and/or other excipients may be reduced accordingly to accommodate the amount of lubricant(s) added in order to keep the overall unit weight of the dosage form unchanged.

In some embodiments, glidants are used. Examples of glidants include colloidal silicon dioxide, magnesium trisilicate, powdered cellulose, starch, talc, and calcium phosphate, and the like, and mixtures thereof.

In some embodiments, the formulations can include a coating, for example, a film coating. Where film coatings are included, coating preparations may include, for example, a film-forming polymer, a plasticizer, or the like. Also, the coatings may include pigments or opacifiers. Examples of film-forming polymers include hydroxypropyl methylcellulose, hydroxypropyl cellulose, methylcellulose, polyvinyl pyrrolidine, and starches. Examples of plasticizers include polyethylene glycol, tributyl citrate, dibutyl sebecate, castor oil, and acetylated monoglyceride. Furthermore, examples of pigments and opacifiers include iron oxides of various colors, lake dyes of many colors, titanium dioxide, and the like.

In some embodiments, color additives are included. The colorants can be used in amounts sufficient to distinguish dosage form strengths. In some embodiments, color additives approved for use in drugs (see 21 C.F.R. pt. 74) are added to the commercial formulations to differentiate tablet strengths. The use of other pharmaceutically acceptable colorants and combinations thereof is also encompassed by the current disclosure.

The pharmaceutical compositions as disclosed herein may include any other agents that provide improved transfer, delivery, tolerance, and the like. These compositions may include, for example, powders, pastes, jellies, waxes, oils, lipids, lipid (cationic or anionic) containing vesicles (such as Lipofectin®), DNA conjugates, anhydrous absorption pastes, oil-in-water and water-in-oil emulsions, emulsions of Carbowax (polyethylene glycols of various molecular weights), semi-solid gels, and semisolid mixtures containing Carbowax.

In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil, and the like may be used as smoothing agents; coconut oil, olive oil, sesame oil, peanut oil, and soya may be used as suspension agents or lubricants; cellulose acetate phthalate as a derivative of a carbohydrate such as cellulose or sugar, methyl acetatemethacrylate copolymer as a derivative of polyvinyl, or plasticizers such as ester phthalate may be used as suspension agents.

In one embodiment, a pharmaceutical composition as disclosed herein further comprises one or more of preservatives, stabilizers, dyes, sweeteners, fragrances, flavoring agents, and the like. For example, sodium benzoate, ascorbic acid, and esters of p-hydroxybenzoic acid may be included as preservatives. Antioxidants and suspending agents may also be included in the pharmaceutical composition.

In addition to being used as a monotherapy, the compounds and pharmaceutical compositions disclosed herein may also find use in combination therapies. Effective combination therapy may be achieved with a single pharmaceutical composition that includes multiple active ingredients, or with two or more distinct pharmaceutical compositions. Alternatively, each therapy may precede or follow the other by intervals ranging from minutes to months.

In some embodiments, one or more of, or any combination of, the listed excipients can be specifically included or excluded from the pharmaceutical compositions or methods disclosed herein.

Any of the foregoing formulations may be appropriate in treatments and therapies in accordance with the disclosure herein, provided that the one or more active ingredient in the pharmaceutical composition is not inactivated by the formulation and the formulation is physiologically compatible and tolerable with the route of administration (see also Baldrick P., "Pharmaceutical excipient development: the need for preclinical guidance." *Regul. Toxicol. Pharmacol.* 32(2):210-8 (2000); Charman W. N., "Lipids, lipophilic drugs, and oral drug delivery-some emerging concepts." *J. Pharm. Sci.* 89(8):967-78 (2000), and the citations therein for additional information related to formulations, excipients, and carriers well known to pharmaceutical chemists).

In some embodiments, the above excipients can be present in an amount up to about 95% of the total composition weight, or up to about 85% of the total composition weight, or up to about 75% of the total composition weight, or up to about 65% of the total composition weight, or up to about 55% of the total composition weight, or up to about 45% of the total composition weight, or up to about 43% of the total composition weight, or up to about 40% of the total composition weight, or up to about 35% of the total composition weight, or up to about 30% of the total composition weight, or up to about 25% of the total composition weight, or up to about 20% of the total composition weight, or up to about 15% of the total composition weight, or up to about 10% of the total composition weight, or less.

As will be appreciated by those of skill in the art, the amounts of excipients will be determined by drug dosage and dosage form size. In some embodiments disclosed herein, the dosage form size is about 200 mg to 800 mg. In another embodiment disclosed herein, the dosage form size is about 200 mg. In a further embodiment disclosed herein, the dosage form size is about 400 mg. In a further embodiment disclosed herein, the dosage form size is about 800 mg. One skilled in the art will realize that a range of weights may be made and are encompassed by this disclosure.

The pharmaceutical compositions of the present disclosure may be manufactured in a manner that is itself known, e.g., by means of conventional mixing, dissolving, granulating, dragee-making, levigating, emulsifying, encapsulating, entrapping, or tableting processes.

The pharmaceutical compositions of the present disclosure may provide low-dose formulations of the compound of structure (I), or a pharmaceutically acceptable salt thereof, in tablets, film coated tablets, capsules, caplets, pills, gel caps, pellets, beads, or dragee dosage forms. The formulations disclosed herein can provide favorable drug processing qualities, including, for example, rapid tablet press speeds, reduced compression force, reduced ejection forces, blend uniformity, content uniformity, uniform dispersal of color, accelerated disintegration time, rapid dissolution, low friability (preferable for downstream processing such as packaging, shipping, pick-and-pack, etc.) and dosage form physical characteristics (e.g., weight, hardness, thickness, friability) with little variation.

Proper formulation is dependent upon the route of administration chosen. Suitable routes for administering the compound of structure (I), or a pharmaceutically acceptable salt thereof, or a pharmaceutical composition comprising the same, may include, for example, oral, rectal, transmucosal, topical, or intestinal administration; and parenteral delivery, including intramuscular, subcutaneous, intravenous, intramedullary injections, intrathecal, direct intraventricular, intraperitoneal, intranasal, or intraocular injections. The compound of structure (I), or a pharmaceutically acceptable salt thereof, may also be administered in sustained or controlled release dosage forms, including depot injections, osmotic pumps, pills, transdermal (including electrotransport) patches, and the like, for prolonged or timed, pulsed administration at a predetermined rate.

Injectables can be prepared in conventional forms, either as liquid solutions or suspensions, solid forms suitable for solution or suspension in liquid prior to injection, or as emulsions. Suitable excipients may include, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include Hanks' solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit, or almond oils, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, or dispersing agents. Alternatively, the active ingredient may be in powder form for constitution with a suitable vehicle, e.g., sterile pyrogen-free water, before use.

For oral administration, the compound of structure (I), or a pharmaceutically acceptable salt thereof, can be formulated by combining the active compound with pharmaceutically acceptable carriers known in the art. Such carriers enable the compound to be formulated as tablets, film coated tablets, pills, dragees, capsules, liquids, gels, get caps, pellets, beads, syrups, slurries, suspensions, and the like, for oral ingestion by a patient to be treated.

Pharmaceutical preparations for oral use can be obtained by combining the active compound with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; and cellulose preparations such as, for example, maize starch, wheat starch, rice starch, potato starch, gelatin, gum tragacanth, methyl cellulose, hydroxypropylmethyl-cellulose, sodium carboxymethylcellulose, or polyvinylpyrrolidone (PVP). If desired, disintegrating agents may be added, such as the cross-linked polyvinyl pyrrolidone, agar, or alginic acid or a salt thereof such as sodium alginate. Dragee cores having suitable coatings are also within the scope of the disclosure. For this purpose, concentrated sugar solutions may be used, which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, titanium dioxide, lacquer solutions, or suitable organic solvents or solvent mixtures. Dyestuffs or pigments may be added to the tablets or dragee coatings for identification or to characterize different combinations of active compound doses. In addition, stabilizers can be added. In some embodiments, formulations for oral administration are in dosages suitable for such administration. In some embodiments, formulations of the compound of structure (I), or a pharmaceutically acceptable salt thereof, have an acceptable immediate release dissolution profile and a robust, scalable method of manufacture.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, or lubricants such as talc or magnesium stearate, and, optionally, stabilizers. In soft capsules, the active compounds may be dissolved or suspended in suitable liquids, such as fatty oils, liquid paraffin, or liquid polyethylene glycols. In addition, stabilizers may be added.

For buccal administration, the compositions may take the form of tablets or lozenges formulated in a conventional manner.

For administration by inhalation, the compound of structure (I), or a pharmaceutically acceptable salt thereof, is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eye drops, or in gellan gum (Shedden et al., *Clin. Ther.* 23(3):440-50, 2001) or hydrogels (Mayer et al., *Ophthalmologica* 210(2):101-3, 1996); ophthalmic ointments; ophthalmic suspensions, such as microparticulates, drug-containing small polymeric particles that are suspended in a liquid carrier medium (Joshi, *J. Ocul. Pharmacol.* 10(1):29-45, 1994), lipid-soluble formulations (Alm et al., *Prog. Clin. Biol. Res.* 312:447-58, 1989), and microspheres (Mordenti, *Toxicol. Sci.* 52(1):101-6, 1999); and ocular inserts. Such suitable pharmaceutical formulations may be formulated to be sterile, isotonic, and buffered for stability and comfort. Pharmaceutical compositions for intranasal delivery may also include drops and sprays often prepared to simulate in many respects nasal secretions, to ensure maintenance of normal ciliary action. As disclosed in "Remington's Pharmaceutical Sciences," 18th Ed., Mack Publishing Co., Easton, Pa. (1990), and well known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compound of structure (I), or a pharmaceutically acceptable salt thereof, may also be formulated in rectal compositions such as suppositories or retention enemas, e.g., those containing conventional suppository bases such as cocoa butter or other glycerides.

In addition to the formulations described previously, the compound of structure (I), or pharmaceutically acceptable salt thereof, may also be formulated as a depot preparation. Such long acting formulations may be administered by implantation (for example subcutaneously or intramuscularly) or by intramuscular injection. Thus, for example, the compound of structure (I), or a pharmaceutically acceptable salt thereof, may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. The proportions of a co-solvent system may be varied considerably without destroying its solubility and toxicity characteristics. Furthermore, the identity of the co-solvent components may be varied: for example, other low-toxicity nonpolar surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well-known examples of delivery vehicles or carriers for hydrophobic drugs. In some embodiments, certain organic solvents such as dimethylsulfoxide also may be employed.

Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. Molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Methods of Administration

The compound of structure (I), or a pharmaceutically acceptable salt thereof, or pharmaceutical compositions comprising the same, may be administered to the patient by any suitable means. Examples of methods of administration include (a) administration though oral pathways, which includes administration in capsule, tablet, granule, spray, syrup, and other such forms; (b) administration through non-oral pathways such as rectal, vaginal, intraurethral, intraocular, intranasal, and intraauricular, which includes administration as an aqueous suspension, an oily preparation, or the like as a drip, spray, suppository, salve, ointment, or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; and (e) administration topically; as deemed appropriate by those of skill in the art for bringing the compound of structure (I), or pharmaceutically acceptable salt thereof, into contact with living tissue.

Pharmaceutical compositions suitable for administration include compositions where the compound of structure (I), or a pharmaceutically acceptable salt thereof, is contained in an amount effective to achieve its intended purpose. The dose can be tailored to achieve a desired effect, but will depend on such factors as weight, diet, concurrent medication, and other factors that those skilled in the medical arts will recognize. More specifically, a therapeutically effective amount means an amount of compound effective to provide a therapeutic benefit to the subject being treated.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will be dependent on many factors including the subject being treated, the severity of the affliction, the manner of administration, and the judgment of the prescribing physician. In one embodiment, the compound of structure (I), or pharmaceutically acceptable salt thereof, may be administered orally or via injection at a dose from 0.001 mg/kg to 2500 mg/kg of the patient's body weight per day. In a further embodiment, the dose range for adult humans is from 0.01 mg to 10 g/day. Tablets or other forms of presentation provided in discrete units may conveniently contain an amount of the compound of structure (I), or a pharmaceutically acceptable salt thereof, that is effective at such dosage or as a multiple of the same, for instance, units containing 5 mg to 1000 mg, usually from about 100 mg to about 800 mg. The dose employed will depend on a number of factors, including the age and sex of the patient, the precise disorder being treated, and its severity. Also, the route of administration may vary depending on the condition and its severity.

In cases wherein a salt is administered, dosages may be calculated as the dose of the free base.

In some embodiments, the dose range of the pharmaceutical composition administered to the patient can be from about 0.01 mg/kg to about 1000 mg/kg of the patient's body weight. The dosage may be a single one or a series of two or more given in the course of one or more days, as is needed by the patient.

In some embodiments, the daily dosage regimen for an adult human patient may be, for example, an oral dose of each active ingredient of between 0.1 mg and 2000 mg, or between 1 mg and 1500 mg, or between 5 mg to 1000 mg. In other embodiments, an oral dose of each active ingredient of between 1 mg and 1000 mg, between 50 mg and 900 mg, and between 100 mg to 800 mg is administered. In some embodiments, the oral dose is administered 1 to 4 times per day. In another embodiment, compositions of the compound of structure (I), or a pharmaceutically acceptable salt thereof, may be administered by continuous intravenous infusion, at a dose of each active ingredient up to 1000 mg per day. In some embodiments, the compound of structure (I), or a pharmaceutically acceptable salt thereof, will be administered for a period of continuous therapy, for example for a week or more, or for months or years.

In some embodiments, the dosing regimen of the compound of structure (I), or a pharmaceutically acceptable salt thereof, is administered for a period of time, which time period can be, for example, from at least about 4 weeks to at least about 8 weeks, from at least about 4 weeks to at least about 12 weeks, from at least about 4 weeks to at least about 16 weeks, or longer. The dosing regimen of the compound of structure (I), or pharmaceutically acceptable salt thereof, can be administered three times a day, twice a day, daily, every other day, three times a week, every other week, three times per month, once monthly, substantially continuously, or continuously.

In cases of local administration or selective uptake, the effective local concentration of the drug may not be related to plasma concentration. The amount of composition administered may be dependent on the subject being treated, on the subject's weight, the severity of the affliction, and the manner of administration.

In one embodiment, the present disclosure relates to a method of using an effective amount of the compound of structure (I) or pharmaceutically acceptable salt thereof in the treatment of endothelin-dependent or angiotensin II-dependent disorders in a patient comprising administering to the patient a dosage of the compound of structure (I) or pharmaceutically acceptable salt thereof containing an amount of about 10 mg to about 1000 mg, of drug per dose, orally, at a frequency of three times per month, once monthly, once weekly, once every three days, once every two days, once per day, twice per day, three times per day, substantially continuously, or continuously, for the desired duration of treatment.

In another embodiment, the present disclosure provides a method of using an effective amount of the compound of structure (I) or pharmaceutically acceptable salt thereof in the treatment of endothelin-dependent or angiotensin-II dependent disorders in a patient comprising administering to the patient a dosage containing an amount of about 100 mg to about 1000 mg, of drug per dose, orally, at a frequency of three times per month, once monthly, once weekly, once every three days, once every two days, once per day, twice per day, or three times per day, for the desired duration of treatment.

In yet another embodiment, the present disclosure provides a method of using an effective amount of the compound of structure (I) or pharmaceutically acceptable salt thereof in the treatment of endothelin-dependent or angiotensin II-dependent disorders in a patient comprising administering to the patient a dosage containing an amount of about 200 mg of drug per dose, orally, at a frequency of three times per month, once monthly, once weekly, once every three days, once every two days, once per day, twice per day, or three times per day, for the desired duration of treatment.

In a further embodiment, the present disclosure provides a method of using an effective amount of the compound of structure (I) or pharmaceutically acceptable salt thereof in the treatment of endothelin-dependent or angiotensin II-dependent disorders in a patient comprising administering to the patient a dosage containing an amount of about 400 mg of drug per dose, orally, at a frequency of three times per month, once monthly, once weekly, once every three days, once every two days, once per day, twice per day, or three times per day, for the desired duration of treatment.

In a further embodiment, the present disclosure provides a method of using an effective amount of the compound of structure (I) or pharmaceutically acceptable salt thereof in the treatment of endothelin-dependent or angiotensin II-dependent disorders in a patient comprising administering to the patient a dosage containing an amount of about 800 mg of drug per dose, orally, at a frequency of three times per month, once monthly, once weekly, once every three days, once every two days, once per day, twice per day, or three times per day, for the desired duration of treatment.

In a further embodiments, the present disclosure provides a method of using an effective amount of the compound of structure (I) or pharmaceutically acceptable salt thereof in the treatment of endothelin-dependent or angiotensin II-dependent disorders in a patient comprising administering to the patient a dosage from about 0.1 mg/kg to about 100 mg/kg, or from about 0.2 mg/kg to about 50 mg/kg, or from about 0.5 mg/kg to about 25 mg/kg of body weight (or from about 1 mg to about 2500 mg, or from about 100 mg to about 800 mg) of active compound per day, which may be administered in a single dose or in the form of individual divided doses, such as from 1 to 4 times per day.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in a form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising the compound of structure (I), or pharmaceutically acceptable salt thereof, formulated in a compatible pharmaceutical carrier may also be prepared, placed in an appropriate container, and labeled for treatment of an indicated condition.

EXAMPLES

Example 1

Proteinuria as a Predictor of Long-Term Renal Survival

In patients with focal segmental glomerulosclerosis (FSGS), proteinuria is currently used as an indicator of disease activity. To determine if proteinuria can be used to predict long-term renal survival in patients with FSGS, prospective data on proteinuria, estimated Glomerular Filtration Rate (eGFR), and end-stage renal disease (ESRD) status were collected on 118 FSGS patients from the Nephrotic Syndrome Study Network (NEPTUNE). Urine protein to creatinine ("UP/C") ratios were measured at the time of biopsy and every four months for the first year after biopsy.

Kaplan-Meier analyses were generated to estimate the effect of proteinuria on subsequent progression to ESRD or 40% reduction in eGFR. Proteinuria was categorized by conventional definitions of complete (UP/C ratio <0.3 g/g) and partial (50% reduction in UP/C ratio and UP/C ratio <3.5 g/g) remission. ROC analyses were performed to determine other important thresholds of proteinuria. Results were replicated and validated using 109 patients from the focal segmental glomerulosclerosis clinical trial (FSGS-CT).

Figure 1B:
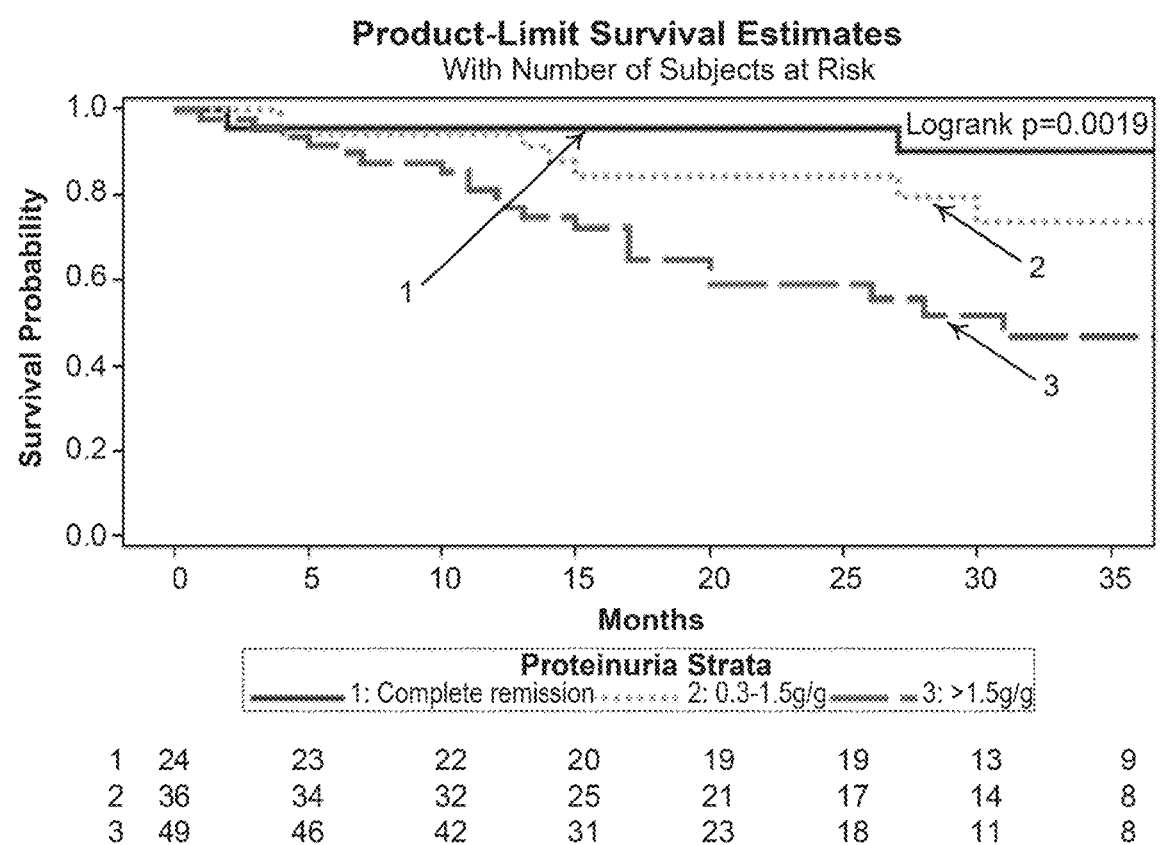
FIG. 1B. Proteinuria Strata and Progression to Subsequent ESRD or 40% Reduction in eGFR for FSGS-CT data (n=109). The y-axis shows survival probability for patients showing complete remission (UP/C ratio less than 0.3 g/g; proteinuria strata "1"), proteinuria levels of 0.3 to 1.5 g/g (proteinuria strata "2"), or proteinuria levels of greater than 1.5 g/g (proteinuria strata "3"). The x-axis shows time in months.

In NEPTUNE, 39 patients progressed to ESRD or 40% reduction in eGFR during follow-up. Reaching a complete remission, but not necessarily a partial remission, was associated with a decreased risk of disease progression. Using ROC analyses, patients with a UP/C ratio <1.5 g/g were identified as less likely to progress (FIG. 1A and FIG. 1B).

Reaching either a complete remission of proteinuria or a UP/C ratio <1.5 g/g was associated with better long-term outcomes in patients with FSGS.

Example 2

Treatment of Focal Segmental Glomerulosclerosis (FSGS) with Sparsentan

DUET trial is a phase 2, double-blind, randomized, active-control, dose-escalation study (NCT01613118) that evaluates the efficacy and safety of sparsentan as a treatment for primary focal segmental glomerulosclerosis (FSGS), a rare disorder characterized by massive proteinuria and progressive loss of kidney function. Patients (ranging in age from 8 years to 75 years) with biopsy-proven primary FSGS (or documentation of a genetic mutation in a podocyte protein associated with the disease) having baseline urine protein to creatinine ("UP/C") ratios greater than 1 g/g and estimated glomerular filtration rates greater than 30 ml/min were eligible for the study. The inclusion criteria also included a mean seated blood pressure >100/10 mmHg and <145/96 mmHg for patients aged 18 years or older, or, for patients aged <18 years of age, a mean seated blood pressure of >90/60 mmHg and <95th percentile for age, gender, and height. The inclusion criteria included an allowance for a stable dose of immunosuppressive medication for ≥1 month. Exclusion criteria included secondary FSGS; significant medical conditions related to cardiac, hepatic, or immune function; body mass index >40 mg/m$^2$ for adults or in the 99th percentile plus 5 for pediatric patients; hematocrit <27% or hemoglobin <9 m/dL; serum potassium >5.5 mEq/L; and women who were pregnant, breastfeeding, or of child-bearing potential who were unwilling to use two methods of contraception.

Patients who signed consent and met all inclusion and exclusion criteria during the screening phase underwent a 2-week angiotensin receptor blocker (ARB) and angiotensin converting enzyme (ACE) inhibitor washout period before being randomly assigned to one of the three escalating dose cohorts receiving sparsentan (200 mg/day; 400 mg/day; and 800 mg/day) or a fixed maximal dose of active control (the ARB irbesartan, at 300 mg/day) in a 3:1 ratio within each cohort. The primary endpoint was the change in UP/C ratio (determined as a measure of urinary protein excretion) from baseline. The proportion of patients achieving UP/C ratio ≤1.5 g/g with >40% reduction in UP/C ratio at Week 8, a modified responder analysis, was evaluated as secondary endpoint.

After the completion of an 8-week double-blind period, the patients continued sparsentan treatment on their assigned doses in an open-label extension for 136 additional weeks. Irbesartan control arm patients were offered sparsentan treatment at the dose they would have received according to the double-blind dose group in which they were enrolled.

The analysis of the primary endpoint included 96 randomized patients who received at least one dose of the study drug, and had both baseline and week 8 UP/C ratio values (i.e., had completed 8 weeks of double-blind treatment). The pre-specified analysis order was (1) all sparsentan doses vs. irbesartan; (2) sparsentan 800- and 400-mg doses vs. irbesartan; (3) sparsentan 400-mg dose vs. irbesartan; (4) sparsentan 800-mg dose vs. irbesartan.

Figure 2:
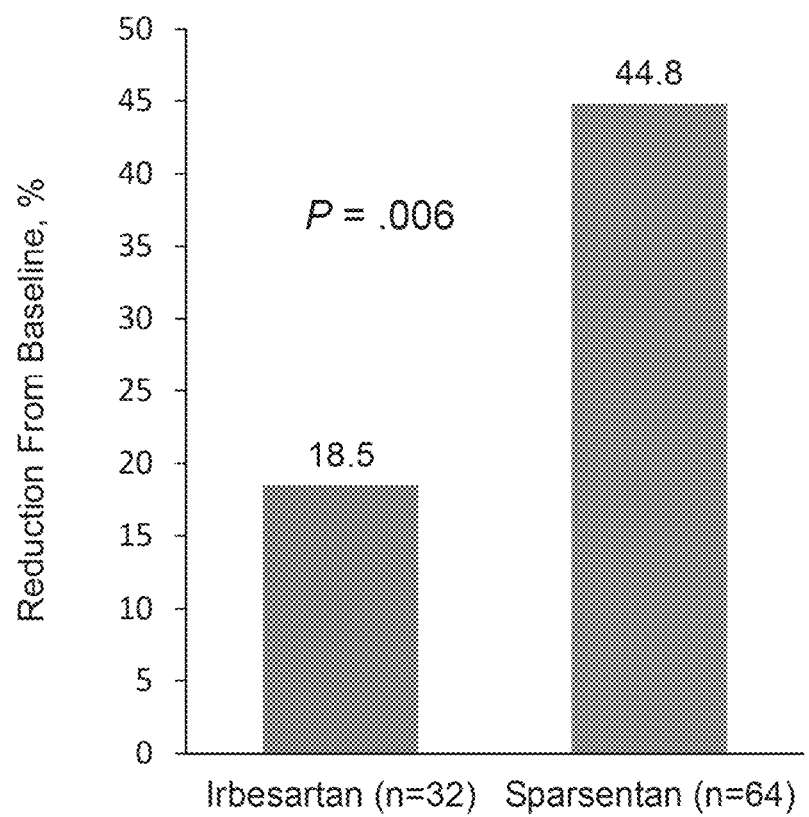
FIG. 2. Reduction in UP/C ratio from baseline for patients treated with sparsentan (all dose cohorts; n=64) and patients treated with irbesartan (n=32). Geometric least squares mean reduction; p-values from analysis of covariance.
Figure 3:
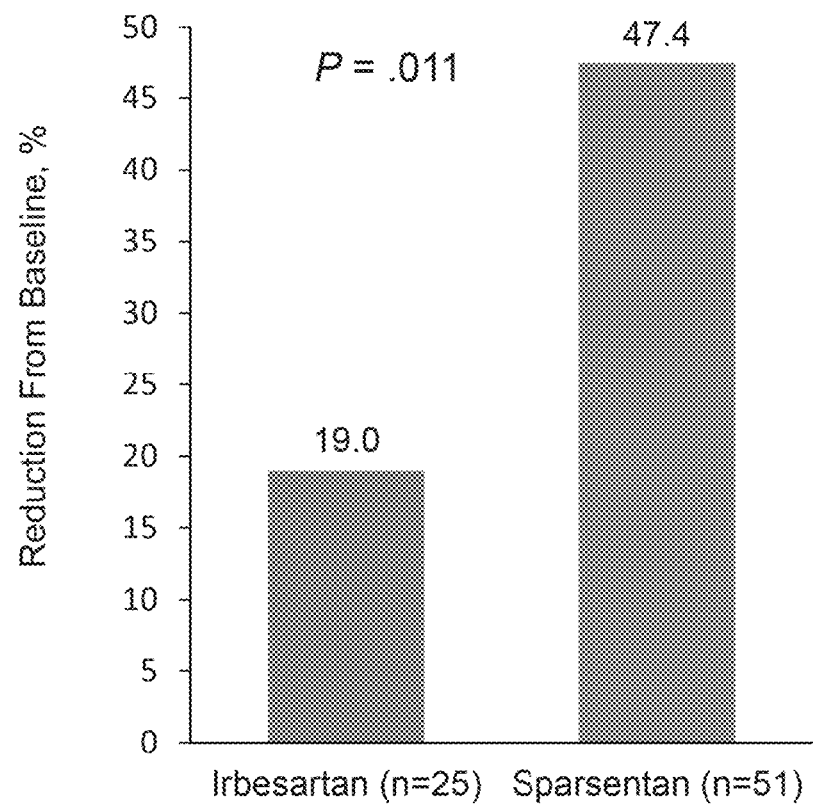
FIG. 3. Reduction in UP/C ratio from baseline for patients treated with sparsentan (200 mg/day and 400 mg/day dose cohorts; n=51) and patients treated with irbesartan (n=25). Geometric least squares mean reduction; p-values from analysis of covariance.

After pooling all sparsentan dose groups, sparsentan-treated patients demonstrated greater decreases in UP/C ratio compared to those treated with irbesartan (45% vs. 19%, p<0.01; Table 1; FIG. 2). A significant reduction was also detected in pooled 400 mg/day to 800 mg/day sparsentan groups (47% vs. 19%, p<0.05; Table 2; FIG. 3).

TABLE 1

Change in UP/C ratio (g/g) from baseline to week 8 for patients treated with 200-800 mg/day sparsentan and patients treated with 300 mg/day irbesartan.

|  | Irbesartan | Sparsentan |
|---|---|---|
| Baseline |  |  |
| n | 32 | 64 |
| mean (SD) | 4.017 (2.6717) | 4.707 (3.7810) |

TABLE 1-continued

Change in UP/C ratio (g/g) from baseline to week 8 for patients treated with 200-800 mg/day sparsentan and patients treated with 300 mg/day irbesartan.

|  | Irbesartan | Sparsentan |
|---|---|---|
| median | 3.265 | 3.620 |
| minimum, maximum | 0.88, 10.73 | 0.43, 18.66 |
| Week 8 |  |  |
| n | 32 | 64 |
| mean (SD) | 3.164 (2.2713) | 3.300 (3.5719) |
| median | 2.405 | 1.980 |
| minimum, maximum | 0.43, 10.19 | 0.12, 14.47 |
| % Change from Baseline to Week 8 |  |  |
| geometric LSmeans | −18.5 | −44.8 |
| 95% CI of % change in geometric LSmeans | (−34.6, 1.7) | (−52.7, −35.7) |
| p-value |  | 0.006 |

TABLE 2

Change in UP/C ratio (g/g) from baseline to week 8 for patients treated with 400-800 mg/day sparsentan and patients treated with 300 mg/day irbesartan.

|  | Irbesartan | Sparsentan |
|---|---|---|
| Baseline |  |  |
| n | 25 | 51 |
| mean (SD) | 3.816 (2.7160) | 4.824 (4.0506) |
| median | 2.970 | 3.530 |
| minimum, maximum | 0.88, 10.73 | 0.43, 18.66 |
| Week 8 |  |  |
| n | 25 | 51 |
| mean (SD) | 2.990 (2.3598) | 3.208 (3.4738) |
| median | 2.390 | 1.900 |
| minimum, maximum | 0.43, 10.19 | 0.12, 14.47 |
| % Change from Baseline to Week 8 |  |  |
| geometric LSmeans | −19.0 | −47.4 |
| 95% CI of % change in geometric LSmeans | (−38.0, 5.9) | (−56.3, −36.9) |
| p-value |  | 0.011 |

The reduction in proteinuria in patients treated with sparsentan was greater that the reduction in patients treated with irbesartan within each cohort, although the within-cohort comparisons were not statistically significant (Table 3).

TABLE 3

Change in UP/C ratio (g/g) from baseline to week 8 for patients treated with 200, 400, or 800 mg/day sparsentan and patients treated with 300 mg/day irbesartan.

| Sparsentan dose cohort | Reduction from Baseline[1] (%) | | p-value[2] |
|---|---|---|---|
|  | Irbesartan | Sparsentan |  |
| All | 18.5 | 44.8 | 0.006 |
|  | (n = 32) | (n = 64) |  |
| 400 mg and 800 mg | 19.0 | 47.4 | 0.011 |
|  | (n = 25) | (n = 51) |  |
| 200 mg | 15.0 | 33.1 | 0.298 |
|  | (n = 7) | (n = 13) |  |

TABLE 3-continued

Change in UP/C ratio (g/g) from baseline to week 8 for patients treated with 200, 400, or 800 mg/day sparsentan and patients treated with 300 mg/day irbesartan.

| Sparsentan dose cohort | Reduction from Baseline[1] (%) | | p-value[2] |
|---|---|---|---|
| | Irbesartan | Sparsentan | |
| 400 mg | 28.1 (n = 17) | 52.7 (n = 21) | 0.056 |
| 800 mg | 9.3 (n = 8) | 41.3 (n = 30) | 0.127 |

[1]Geometric least squares mean reduction.
[2]P-values from analysis of covariance.

Figure 4:
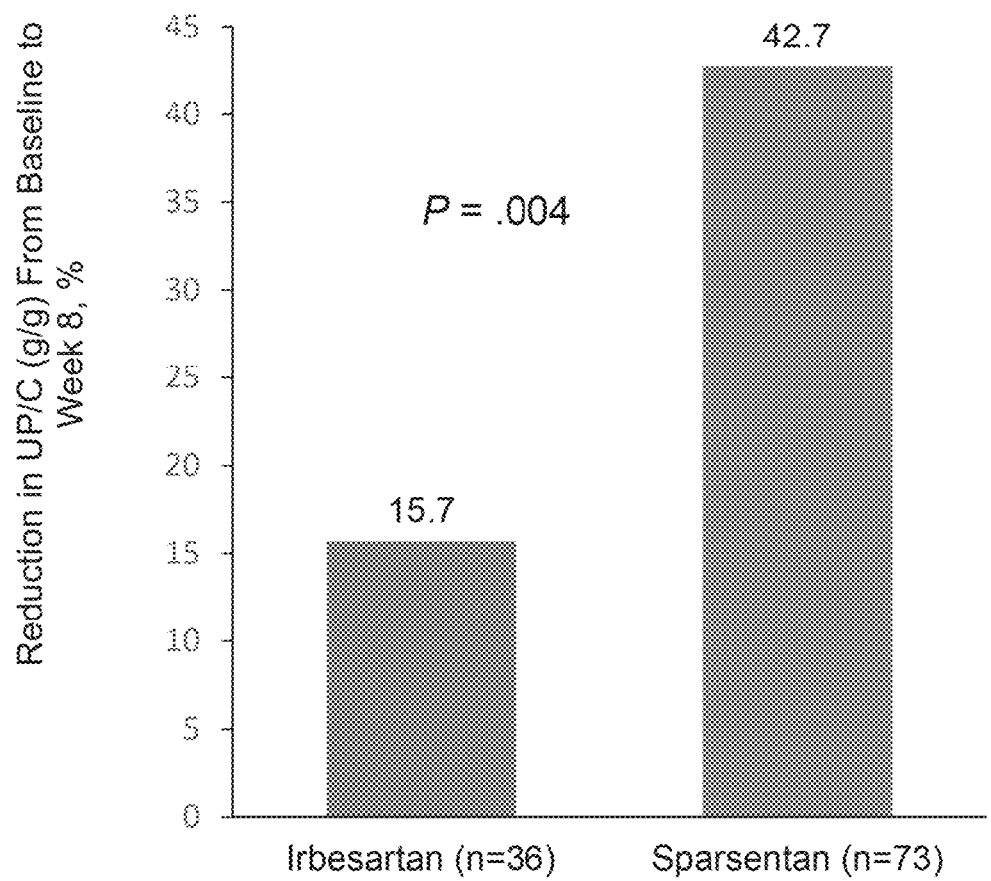
FIG. 4. Intent-to-Treat Analysis of UP/C ratio using imputed data, for all sparsentan dose cohorts. Geometric least squares mean reduction; p-value from analysis of covariance; analyses based on the full dataset.

Baseline or week 8 UP/C ratio data were missing for 9 sparsentan-treated patients and 4 irbesartan-treated patients. An intent-to-treat analysis was conducted, in which the missing data were imputed as zero change in UP/C ratio. Even after imputing the zero values, the change in UP/C ratio from baseline to week 8 was significantly different between sparsentan-treated patients and irbesartan-treated patients (FIG. 4). The results across sparsentan dose cohorts were similar to those observed without imputed data (Table 4).

TABLE 4

Intent-to-treat analysis change in UP/C ratio (g/g) from baseline to week 8 for patients treated with 200, 400, or 800 mg/day sparsentan and patients treated with 300 mg/day irbesartan.

| Sparsentan dose cohort | Reduction from Baseline[1] (%) | | p-value[2] |
|---|---|---|---|
| | Irbesartan | Sparsentan | |
| All | 15.7 (n = 36) | 42.7 (n = 73) | 0.004 |
| 400 mg and 800 mg | 15.9 (n = 28) | 44.8 (n = 60) | 0.008 |
| 200 mg | 13.2 (n = 8) | 33.1 (n = 13) | 0.227 |
| 400 mg | 23.6 (n = 20) | 50.5 (n = 26) | 0.033 |
| 800 mg | 9.7 (n = 8) | 38.4 (n = 34) | 0.161 |

[1]Geometric least squares mean reduction.
[2]P-values from analysis of covariance.

Figure 5:
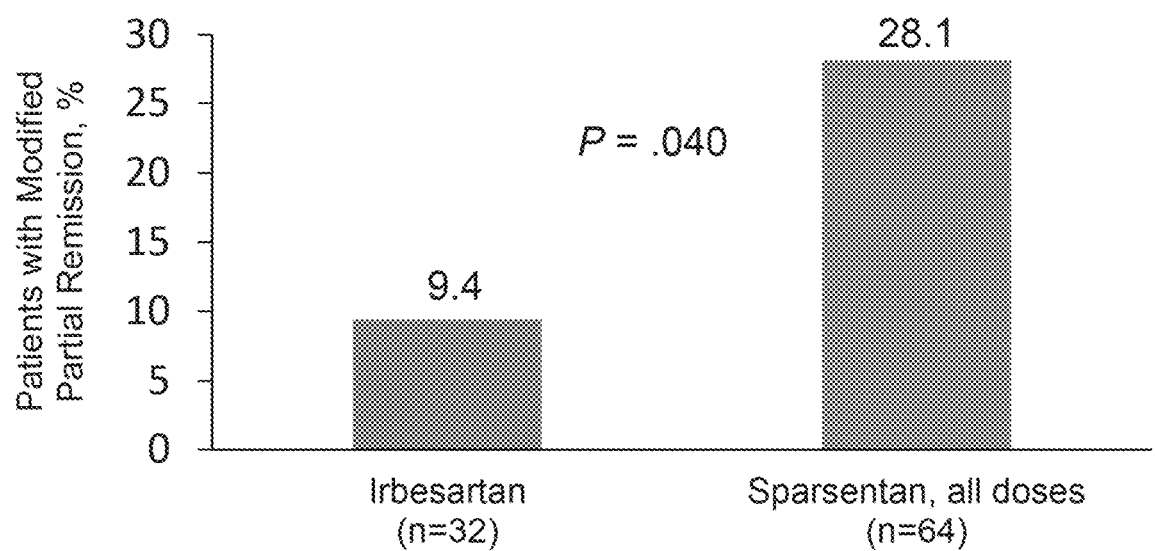
FIG. 5. Percent of patients with Modified Partial Remission (UP/C ratio ≤1.5 g/g and >40% reduction in UP/C ratio) for patients treated with sparsentan (all dose cohorts; n=64) and patients treated with irbesartan (n=32). Geometric least squares mean reduction; p-values from analysis of covariance.

The proportion of patients who achieved UP/C ratio ≤1.5 g/g with >40% reduction was 28% across all sparsentan groups (n=64) and 9% in the irbesartan treatment group (n=32) (Fisher's exact test, p<0.05) (Table 5; FIG. 5).

TABLE 5

Proportion of patients who achieved UP/C ratio ≤1.5 g/g with >40% reduction in patients treated with sparsentan groups and in patients treated with irbesartan.

| Sparsentan dose cohort | Proportion of patients (%) | | p-value[1] |
|---|---|---|---|
| | Irbesartan | Sparsentan | |
| All | 9.4 (n = 32) | 28.1 (n = 64) | 0.040 |
| 400 mg and 800 mg | 12.0 (n = 25) | 31.4 (n = 51) | 0.092 |
| 200 mg | 0.0 (n = 7) | 15.4 (n = 13) | 0.521 |

TABLE 5-continued

Proportion of patients who achieved UP/C ratio ≤1.5 g/g with >40% reduction in patients treated with sparsentan groups and in patients treated with irbesartan.

| Sparsentan dose cohort | Proportion of patients (%) | | p-value[1] |
|---|---|---|---|
| | Irbesartan | Sparsentan | |
| 400 mg | 17.7 (n = 17) | 38.1 (n = 21) | 0.282 |
| 800 mg | 0.0 (n = 8) | 26.7 (n = 30) | 0.164 |

[1]P-values from Fisher's Exact test.

Figure 6A:
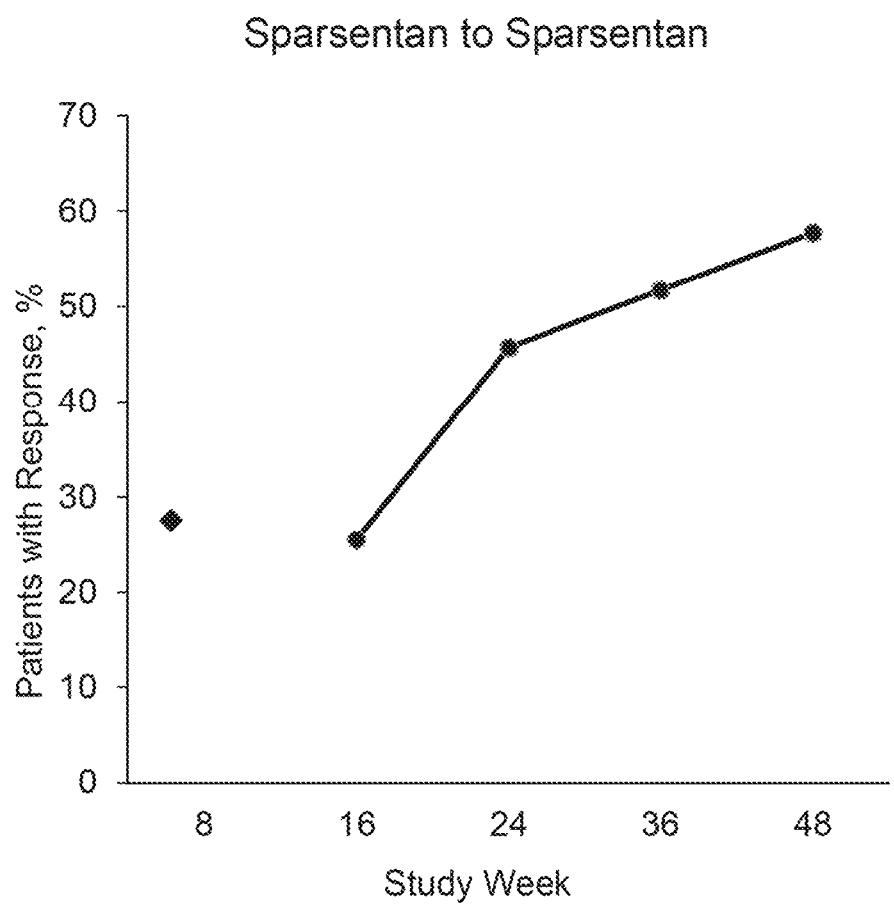
FIG. 6A. Percentage of patients achieving a UP/C ratio ≤1.5 g/g with a >40% reduction in UP/C ratio from baseline during the open-label period (from 8 weeks to 48 weeks), in patients continuing to receive sparsentan. Baseline for the open-label period was defined as the last observation in the double-blind period before the start of the open-label sparsentan treatment (observation at week 8). ◆=24-hour UP/C ratio measurements at week 8; ●=First morning void (spot measure) UP/C ratio on weeks 16 to 48.
Figure 6B:
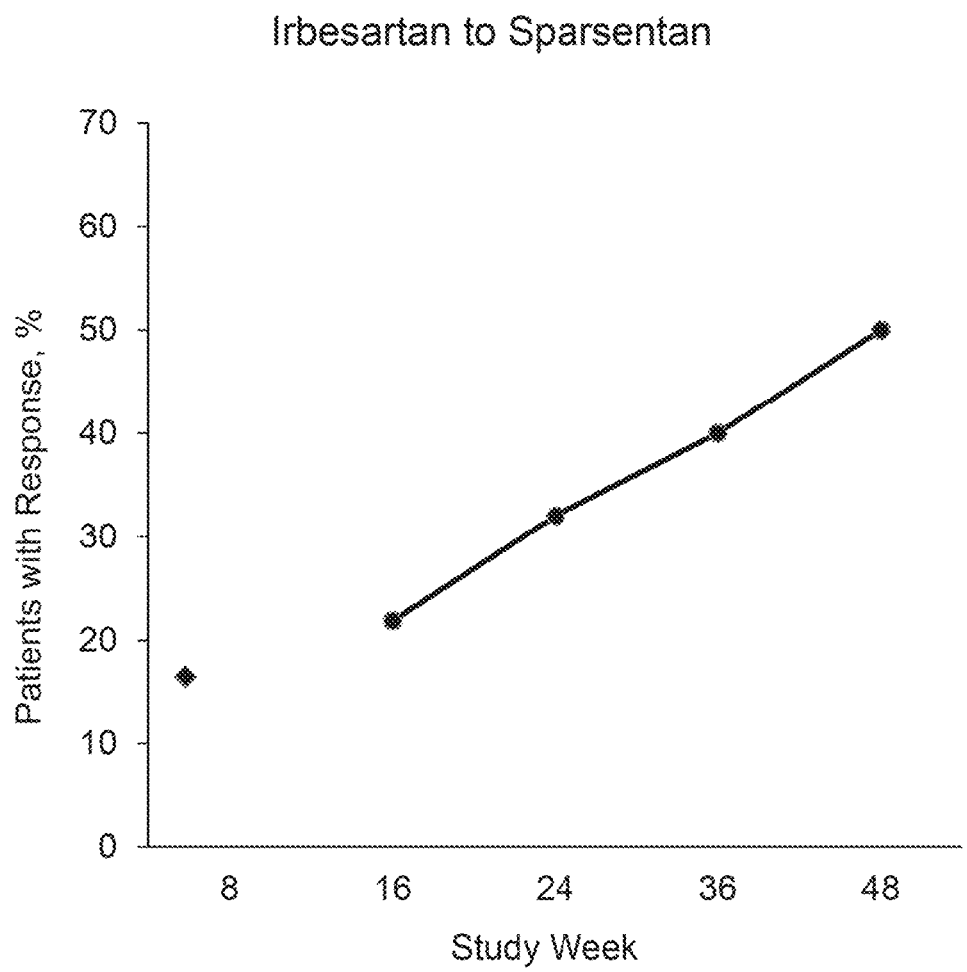
FIG. 6B. Percentage of patients achieving a UP/C ratio ≤1.5 g/g with a >40% reduction in UP/C ratio from baseline during the open-label period (from 8 weeks to 48 weeks), in patients switching from treatment with irbesartan to treatment with sparsentan. Baseline for the open-label period was defined as the last observation in the double-blind period before the start of the open-label sparsentan treatment (observation at week 8). ♦=24-hour UP/C ratio measurements at week 8; ●=First morning void (spot measure) UP/C ratio on weeks 16 to 48.

Complete remission (UP/C ratio <0.3 g/g) occurred in 4 sparsentan-treated patients, but in no irbesartan-treated patients. Additionally, the percentage of patients achieving a UP/C ratio ≤1.5 g/g with a >40% reduction in UP/C ratio increased during the open-label period (from 8 weeks to 48 weeks) in patients continuing to receive sparsentan and in patients that switched from irbesartan to sparsentan (FIGS. 6A and 6B).

Figure 7:
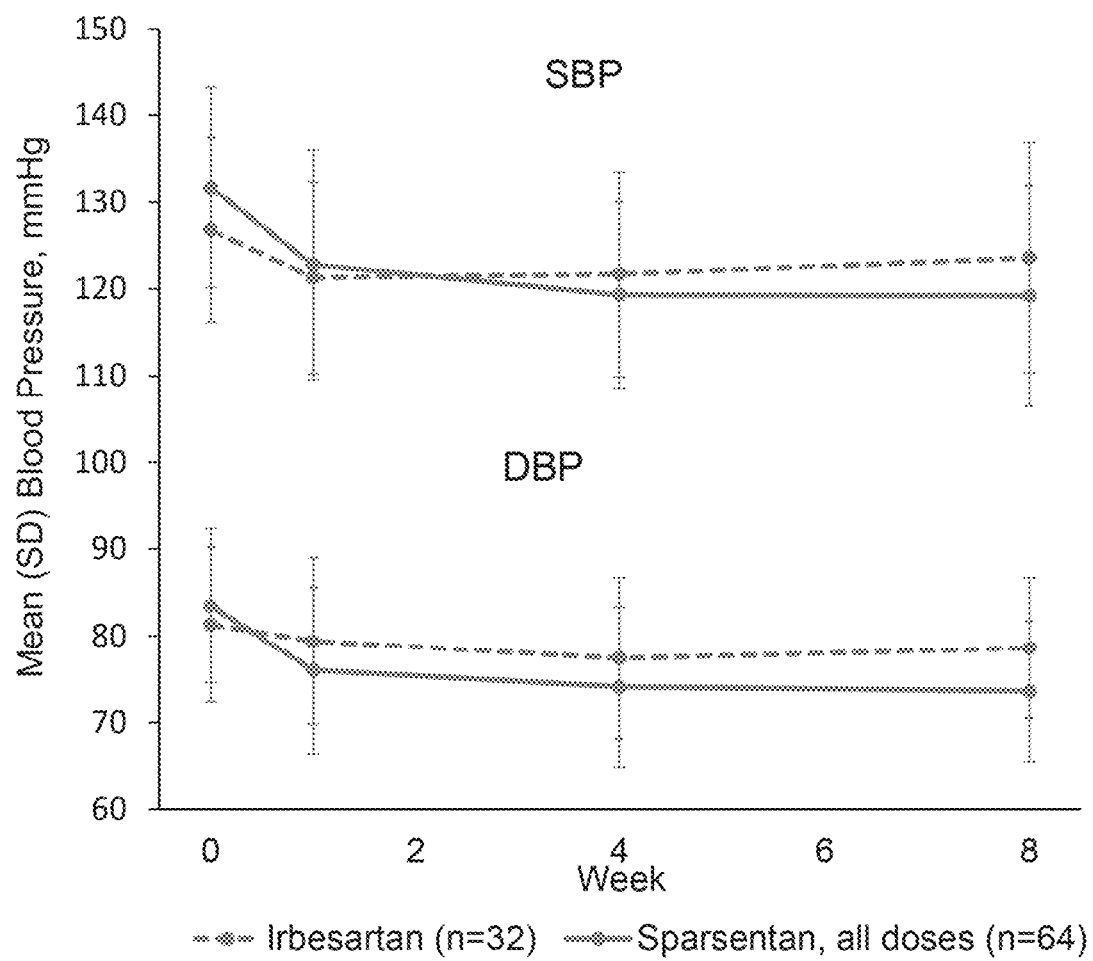
FIG. 7. Blood pressure (systolic blood pressure, "SBP"; diastolic blood pressure, "DBP") for patients treated with irbesartan (n=32) and patients treated with sparsentan (n=64).
Figure 8:
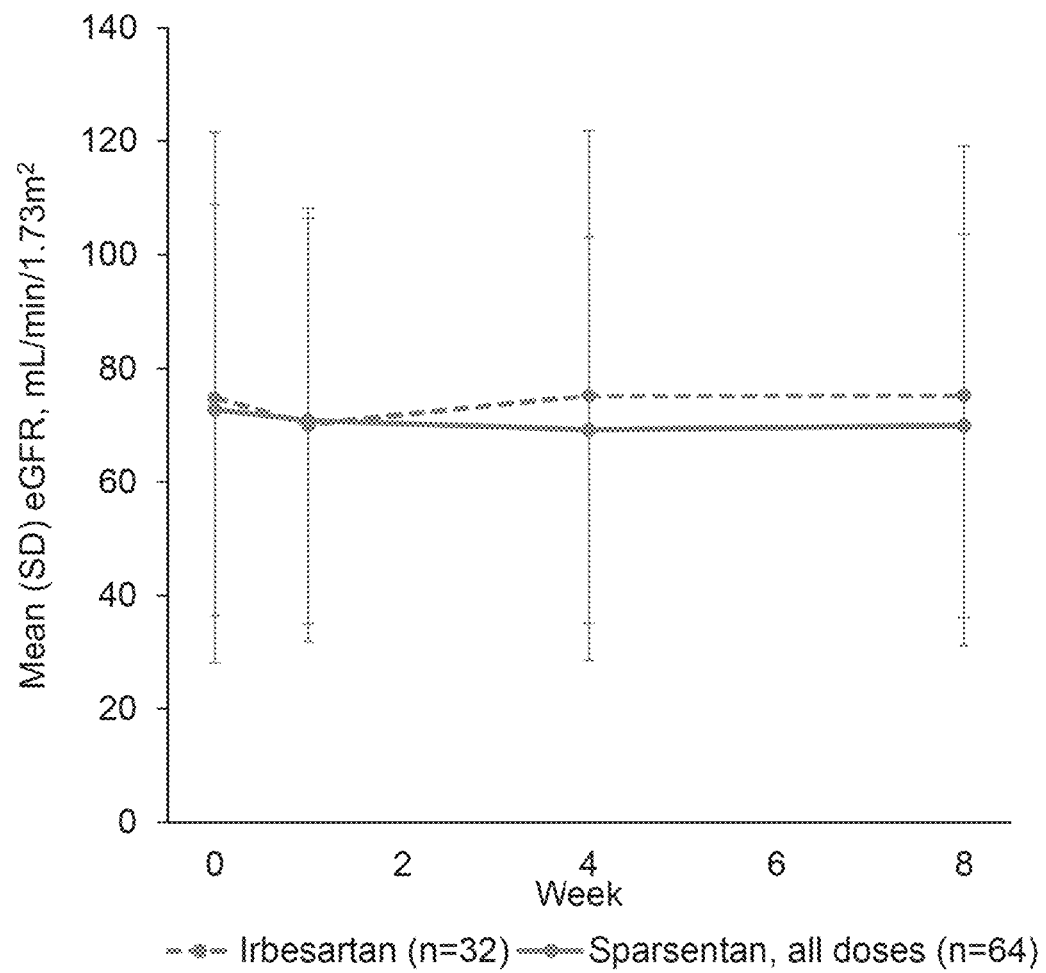
FIG. 8. Estimated Glomerular Filtration Rate (eGFR) for patients treated with irbesartan (n=32) and patients treated with sparsentan (n=64).

Both irbesartan-treated and sparsentan-treated patients showed reductions in mean systolic and diastolic blood pressures relative to baseline values; this reduction was statistically significant for sparsentan-treated patients (FIG. 7). There was no significant change or difference in eGFR (FIG. 8), or in serum potassium, N-terminal pro-B-type natriuretic peptide, or albumin for either treatment groups.

Comparing categories of treatment emergent adverse events showed that the incidence of events was similar between irbesartan-treated and sparsentan-treated patients, except for those events leading to a dose change or interruption (Table 6). The incidences of specific treatment emergent adverse events for which the incidence was greater than 5% across all patients are shown in Table 7. Symptoms such as headache, dizziness, and edema may be associated with hypotension and some of those symptoms were more frequent in patients treated with sparsentan relative to those patients treated with irbesartan. However, there was no significant different between irbesartan-treated patients and sparsentan-treated patients in the worsening of existing edema (Table 8).

TABLE 6

Percent of patients having treatment emergent adverse effects during treatment with irbesartan or sparsentan.

| | Irbesartan (n = 36) | Sparsentan, All Doses (n = 73) |
|---|---|---|
| Any | 72.2 | 76.7 |
| Drug-related | 36.1 | 43.8 |
| Serious | 2.8 | 2.7 |
| Leading to dose change or interruption | 8.3 | 23.3 |
| Leading to drug discontinuation | 2.8 | 4.1 |
| Leading to study withdrawal | 2.8 | 2.7 |
| Death | 0 | 0 |

TABLE 7

Percent of patients having treatment emergent adverse effects during treatment with irbesartan or sparsentan, for specific events having incidences greater than 5%.

| | Irbesartan (n = 36) | Sparsentan, All Doses (n = 73) |
|---|---|---|
| Headache | 19.4 | 19.2 |
| Hypotension/orthostatic hypotension | 8.3 | 16.4 |
| Dizziness | 11.1 | 13.7 |
| Edema/edema peripheral | 2.8 | 12.3 |
| Nausea | 8.3 | 12.3 |
| Diarrhea | 2.8 | 8.2 |
| Vomiting | 2.8 | 8.2 |
| Upper abdominal pain | 5.6 | 5.5 |
| Cough | 5.6 | 4.1 |
| Fatigue | 11.1 | 4.1 |
| Nasal congestion | 11.1 | 2.7 |
| Upper respiratory tract infection | 5.6 | 2.7 |
| Muscle spasms | 5.6 | 0 |

TABLE 8

Severity of edema at baseline and at week 8 in patients treated with irbesartan and in patients treated with sparsentan (p-value = NS).

| | Patients with Edema During the Double-Blind Period, % | | | |
|---|---|---|---|---|
| Edema | Irbesartan | | Sparsentan, All Doses | |
| Severity Grade | Baseline (n = 29) | Week 8 (n = 28) | Baseline (n = 53) | Week 8 (n = 60) |
| 0 | 76 | 86 | 66 | 65 |
| 1+ to 2+ | 21 | 14 | 32 | 30 |
| 3+ to 4+ | 3 | 0 | 2 | 5 |

In summary, dual AngII and ET inhibition with sparsentan reduced proteinuria in patients with FSGS with a significantly greater antiproteinuric effect compared to monoinhibition of AngII with the ARB irbesartan.

Example 3

Variable-Dosing Regimen for Treatment of Focal Segmental Glomerulosclerosis (FSGS) with Sparsentan Patients administered therapeutically effective doses of sparsentan may exhibit decreased proteinuria. However, reduced blood pressure upon treatment with high doses of sparsentan may also result in hypotension. Accordingly, it may be desirable to initially administer a lower dose of sparsentan and then increase the dose if no change in blood pressure is observed after the low-dose treatment.

Patients with FSGS are administered sparsentan at 400 mg/day for the first 2 weeks. After 2 weeks of treatment, tolerance of this initial dose is evaluated prior to escalating the dose of sparsentan to 800 mg/day. Patients who have blood pressure measurements >90/60 mmHg after treatment with sparsentan at 400 mg/day for 2 weeks are administered a dose of sparsentan of 800 mg/day and continue at this dose level. Patients who exhibit asymptomatic BP≤90/60 mmHg or present with clinical symptoms of orthostatic hypotension, but otherwise tolerate the initial dose after 2 weeks, continue taking the 400 mg/day dose.

All of the U.S. patents, U.S. patent application publications, U.S. patent applications, foreign patents, foreign patent applications, and non-patent publications referred to in this specification or listed in the Application Data Sheet, including U.S. Provisional Patent Application Nos. 62/407,860 filed on Oct. 13, 2016 and 62/423,079 filed on Nov. 16, 2016, are incorporated herein by reference, in their entirety.

The various embodiments described above can be combined to provide further embodiments. Aspects of the embodiments can be modified, if necessary, to employ concepts of the various patents, applications, and publications to provide yet further embodiments. These and other changes can be made to the embodiments in light of the above-detailed description.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of treating Alport syndrome comprising administering to a subject in need thereof a pharmaceutical composition comprising a compound having structure (I),

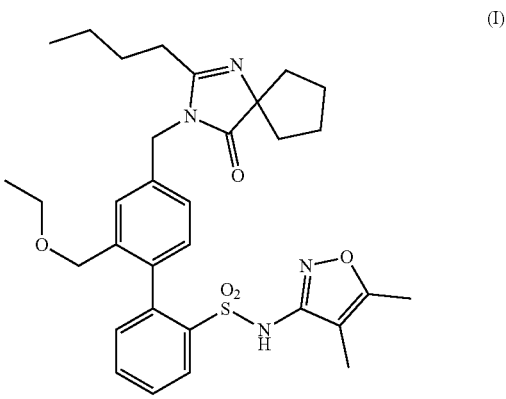 [SMILES: CCCCC1=NC2(CCCC2)C(=O)N1Cc1ccc(-c2ccccc2S(=O)(=O)Nc2noc(C)c2C)c(COCC)c1]

(I)

or a pharmaceutically acceptable salt thereof.

2. The method according to claim 1, wherein said pharmaceutical composition is administered to the subject
   (i) in an amount sufficient to achieve a urine protein to creatinine ("UP/C") ratio of less than or equal to 1.5 g/g;
   (ii) in an amount sufficient to achieve or maintain a UP/C ratio of less than or equal to 1.5 g/g; or
   (iii) at a dosing regimen sufficient to achieve or maintain a UP/C ratio of less than or equal to 1.5 g/g.

3. The method according to claim 1, wherein the pharmaceutical composition is administered to said subject over an administration period in an amount sufficient to achieve or maintain a UP/C ratio of less than or equal to 1.5 g/g for at least a portion of said administration period.

4. The method according to claim 1, wherein said subject has, or has had, a UP/C ratio greater than 1.5 g/g prior to administration of said pharmaceutical composition.

5. The method according to claim 1, wherein said pharmaceutical composition is administered to said subject for a period of 8 weeks, 26 weeks, or 8 months.

6. The method according to claim 1, wherein the amount of said compound having structure (I), or pharmaceutically acceptable salt thereof, administered to said subject is from about 50 mg/day to about 1000 mg/day.

7. The method according to claim 1, wherein the amount of said compound having structure (I), or pharmaceutically acceptable salt thereof, administered to said subject is from about 200 mg/day to about 800 mg/day.

8. The method according to claim 1, wherein the amount of said compound having structure (I), or pharmaceutically acceptable salt thereof, administered to said subject is about 200 mg/day.

9. The method according to claim 1, wherein the amount of said compound having structure (I), or pharmaceutically acceptable salt thereof, administered to said subject is about 400 mg/day.

10. The method according to claim 1, wherein the amount of said compound having structure (I), or pharmaceutically acceptable salt thereof, administered to said subject is about 800 mg/day.

11. The method according to claim 1, wherein said administering comprises (1) an initial administration of said compound having structure (I), or a pharmaceutically acceptable salt thereof, to said subject at an initial dose; and (2) after said initial administration, a subsequent administration of said compound having structure (I), or a pharmaceutically acceptable salt thereof, to said subject at a subsequent dose, wherein said subsequent dose is greater than said initial dose.

12. The method according to claim 11, wherein said initial dose is 400 mg/day and said subsequent dose is 800 mg/day.

13. The method according to claim 11, wherein said initial dose is 200 mg/day and said subsequent dose is 400 mg/day.

14. The method according to claim 13, wherein said subject is a child weighing less than 50 kg.

15. The method according to claim 11, wherein said initial administration has a duration of 2 weeks.

16. The method according to claim 11, wherein the method further comprises measuring the blood pressure of said subject before the subsequent administration.

17. The method according to claim 1, wherein said compound has structure (I).

18. The method according to claim 1, further comprising administering to said subject one or more additional therapeutic agents.

* * * * *